United States Patent
Mino et al.

(10) Patent No.: US 12,303,196 B2
(45) Date of Patent: May 20, 2025

(54) OPHTHALMIC APPARATUS, METHOD OF CONTROLLING SAME, AND RECORDING MEDIUM

(71) Applicant: Topcon Corporation, Tokyo (JP)

(72) Inventors: Toshihiro Mino, Oakland, NJ (US); Jongsik Kim, Fort Lee, NJ (US); Dawei Li, Oakland, NJ (US); Zhenguo Wang, Ridgewood, NJ (US); Kinpui Chan, Ridgewood, NJ (US)

(73) Assignee: TOPCON CORPORATION, Tokyo (JP)

(*) Notice: Subject to any disclaimer, the term of this patent is extended or adjusted under 35 U.S.C. 154(b) by 571 days.

(21) Appl. No.: 17/692,231

(22) Filed: Mar. 11, 2022

(65) Prior Publication Data

US 2022/0192488 A1    Jun. 23, 2022

Related U.S. Application Data

(63) Continuation of application No. PCT/JP2020/033560, filed on Sep. 4, 2020.

(Continued)

(51) Int. Cl.
*A61B 3/14*    (2006.01)
*A61B 3/117*    (2006.01)
(Continued)

(52) U.S. Cl.
CPC ............. *A61B 3/117* (2013.01); *A61B 3/12* (2013.01); *A61B 3/14* (2013.01); *H04N 23/72* (2023.01); *G03B 9/28* (2013.01)

(58) Field of Classification Search
CPC ......... A61B 3/12; A61B 3/1208–3/125; A61B 3/102

(Continued)

(56) References Cited

U.S. PATENT DOCUMENTS 4,422,736 A * 12/1983 Nunokawa ............. A61B 3/156
351/207
4,579,430 A * 4/1986 Bille .................... A61B 5/6821
606/4

(Continued)

FOREIGN PATENT DOCUMENTS

EP  3738501 A1  11/2020
JP  61-293430 A  12/1986

(Continued)

OTHER PUBLICATIONS

Extended European search report issued on Sep. 11, 2023, in corresponding European patent Application No. 20862803.2, 10 pages.

(Continued)

*Primary Examiner* — Zachary W Wilkes
(74) *Attorney, Agent, or Firm* — XSENSUS LLP

(57) ABSTRACT

An ophthalmic apparatus includes an illumination optical system, an imaging optical system, and a controller. The illumination optical system is configured to generate illumination light using light from a light source, and to illuminate a changeable illumination region on a predetermined site of a subject's eye with the illumination light having a light intensity corresponding to a size of the illumination region. The imaging optical system is configured to guide returning light of the illumination light from the subject's eye to a light receiving surface of an image sensor. The controller is configured to control the image sensor to set an opening range so as to overlap an illumination range of the returning light on the light receiving surface corresponding to the illumination region and to capture a light receiving result obtained by a light receiving element in the set opening range.

21 Claims, 19 Drawing Sheets

Related U.S. Application Data

(60) Provisional application No. 62/898,898, filed on Sep. 11, 2019.

(51) Int. Cl.
  *A61B 3/12* (2006.01)
  *H04N 23/72* (2023.01)
  *G03B 9/28* (2021.01)

(58) Field of Classification Search
  USPC .................................................. 351/205–221
  See application file for complete search history.

(56) References Cited

U.S. PATENT DOCUMENTS

| | | | |
|---|---|---|---|
| 7,331,669 B2 | 2/2008 | Elsner | |
| 7,621,638 B2* | 11/2009 | Su | A61B 3/12 362/302 |
| 7,831,106 B2 | 11/2010 | Elsner et al. | |
| 8,100,531 B2* | 1/2012 | Liesfeld | A61B 3/12 351/207 |
| 8,237,835 B1 | 8/2012 | Muller | |
| 8,488,895 B2 | 7/2013 | Muller et al. | |
| 9,089,290 B2* | 7/2015 | Umekawa | A61B 3/12 |
| 9,237,845 B2* | 1/2016 | Numajiri | A61B 3/113 |
| 9,386,920 B2* | 7/2016 | Akita | A61B 3/0025 |
| 9,474,443 B2* | 10/2016 | Yoshino | A61B 3/12 |
| 9,549,672 B2* | 1/2017 | Westphal | A61B 3/14 |
| 10,582,852 B2* | 3/2020 | Bublitz | A61B 3/1208 |
| 2008/0123052 A1* | 5/2008 | Su | A61B 3/12 351/221 |
| 2010/0007849 A1 | 1/2010 | Liesfeld et al. | |
| 2012/0089133 A1 | 4/2012 | Liesfeld et al. | |
| 2012/0165905 A1 | 6/2012 | Liesfeld et al. | |
| 2012/0165906 A1 | 6/2012 | Liesfeld et al. | |
| 2013/0162945 A1* | 6/2013 | Tanaami | A61B 3/12 351/206 |
| 2013/0250242 A1* | 9/2013 | Cheng | A61B 3/12 351/207 |
| 2014/0111766 A1* | 4/2014 | Umekawa | A61B 3/12 351/205 |
| 2014/0232987 A1* | 8/2014 | Westphal | A61B 3/14 351/246 |
| 2015/0042951 A1* | 2/2015 | Stanga | A61B 3/12 351/206 |
| 2015/0085252 A1 | 3/2015 | Fujimura et al. | |
| 2015/0092161 A1* | 4/2015 | Akita | A61B 3/0025 351/206 |
| 2015/0374232 A1* | 12/2015 | Yoshino | A61B 3/12 351/206 |
| 2016/0345822 A1 | 12/2016 | Fujimura et al. | |
| 2022/0095913 A1 | 3/2022 | Everett | |

FOREIGN PATENT DOCUMENTS

| | | |
|---|---|---|
| JP | 2009-542271 A | 12/2009 |
| JP | 2010-25495 A | 2/2010 |
| JP | 2013-248376 A | 12/2013 |
| JP | 2014-73205 A | 4/2014 |
| WO | 2019/138916 A1 | 7/2019 |
| WO | 2020/064777 A1 | 4/2020 |

OTHER PUBLICATIONS

International Search Report and Written Opinion mailed on Oct. 20, 2020, received for PCT Application PCT/JP2020/033560, filed on Sep. 4, 2020, 8 pages including English Translation.

* cited by examiner

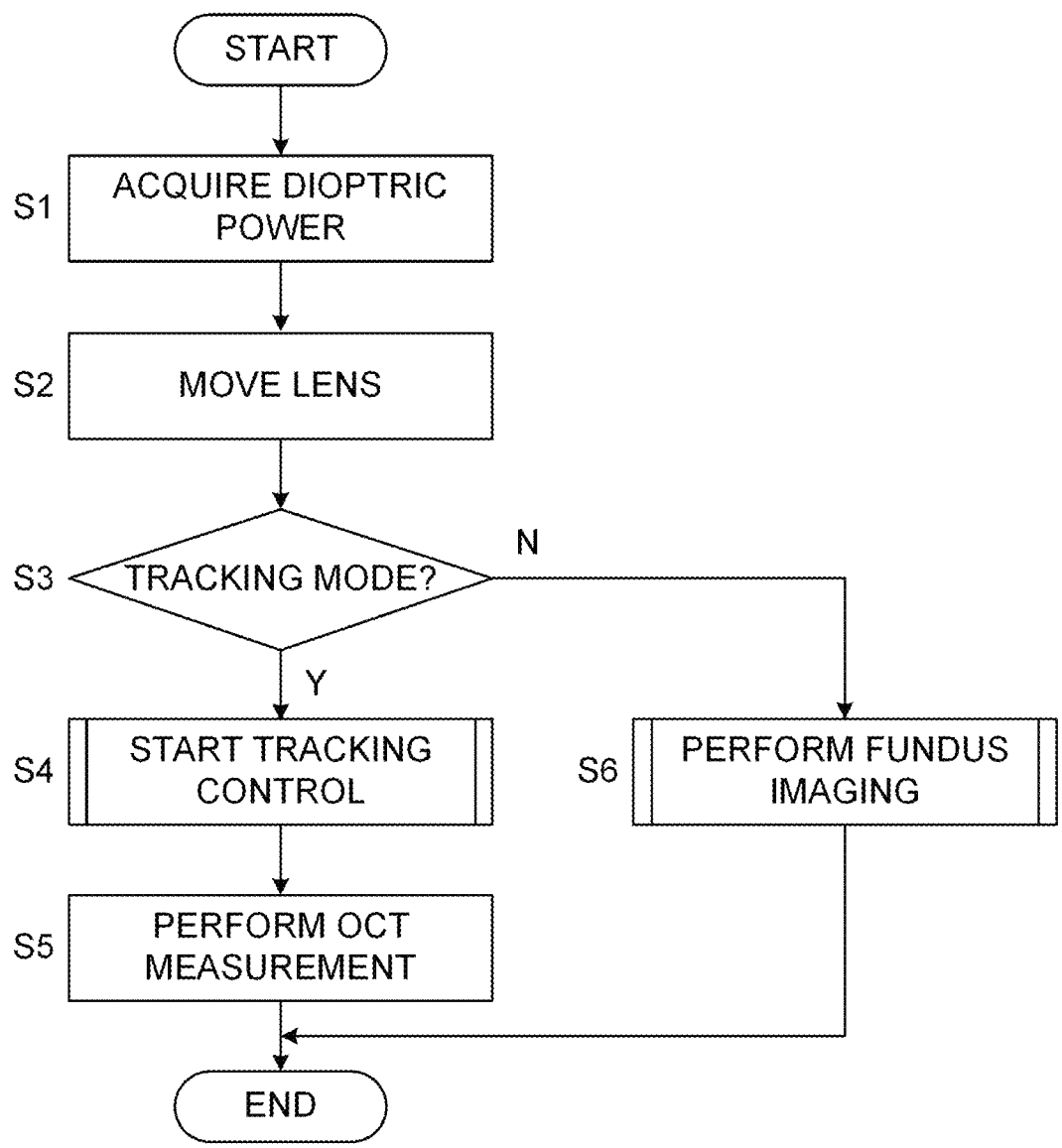

OPHTHALMIC APPARATUS, METHOD OF CONTROLLING SAME, AND RECORDING MEDIUM

CROSS-REFERENCE TO RELATED APPLICATIONS

The present application is a continuation application of International Patent Application No. PCT/JP2020/033560, filed Sep. 4, 2020, which claims priority to U.S. Provisional Application No. 62/898,898, filed Sep. 11, 2019. The contents of these applications are incorporated herein by reference in their entirety.

FIELD

The disclosure relates to an ophthalmic apparatus, a method of controlling the same, and a recording medium.

BACKGROUND

In recent years, screening tests have been performed using ophthalmic apparatuses. Such ophthalmic apparatuses are expected to be applied to self-examinations, and further downsizing and weight saving of the ophthalmic apparatuses are desired.

For example, U.S. Pat. Nos. 7,831,106 and 8,237,835 disclose ophthalmic apparatuses configured to pattern-illuminate a subject's eye using slit-shaped illumination light and to detect returning light of the illumination light using CMOS (Complementary Metal Oxide Semiconductor) image sensor. This ophthalmic apparatus can acquire images of the subject's eye with a simple configuration, by adjusting the illumination pattern and the timing of light receiving timing using the CMOS image sensor.

SUMMARY

One aspect of embodiments is an ophthalmic apparatus, including: an illumination optical system configured to generate illumination light using light from a light source, and to illuminate a changeable illumination region on a predetermined site of a subject's eye with the illumination light having a light intensity corresponding to a size of the illumination region; an imaging optical system configured to guide returning light of the illumination light from the subject's eye to a light receiving surface of an image sensor; and a controller configured to control the image sensor to set an opening range so as to overlap an illumination range of the returning light on the light receiving surface corresponding to the illumination region and to capture a light receiving result obtained by a light receiving element in the set opening range.

Another aspect of the embodiments is a method of controlling an ophthalmic apparatus including: an illumination optical system configured to generate illumination light using light from a light source, and to illuminate a subject's eye with the illumination light; and an imaging optical system configured to guide returning light of the illumination light from the subject's eye to a light receiving surface of an image sensor. The method of controlling the ophthalmic apparatus includes: an illumination region control step of changing an illumination region of the illumination light on a predetermined site of the subject's eye; a light intensity control step of changing light intensity of the illumination light so as to have a light intensity corresponding to a size of the illumination region changed in the illumination region control step; and an image sensor control step of controlling the image sensor to set an opening range so as to overlap an illumination range of the returning light on the light receiving surface corresponding to the illumination region changed in the illumination region control step and to capture a light receiving result obtained by a light receiving element in the set opening range.

Still another aspect of the embodiments is a computer readable non-transitory recording medium in which a program of causing a computer to execute each step of the method of controlling the ophthalmic apparatus described above is recorded.

BRIEF EXPLANATION OF THE DRAWINGS

FIG. 12 is a flow illustrating an example of an operation of the ophthalmic apparatus according to the first embodiment.

DETAILED DESCRIPTION

Figure 1:
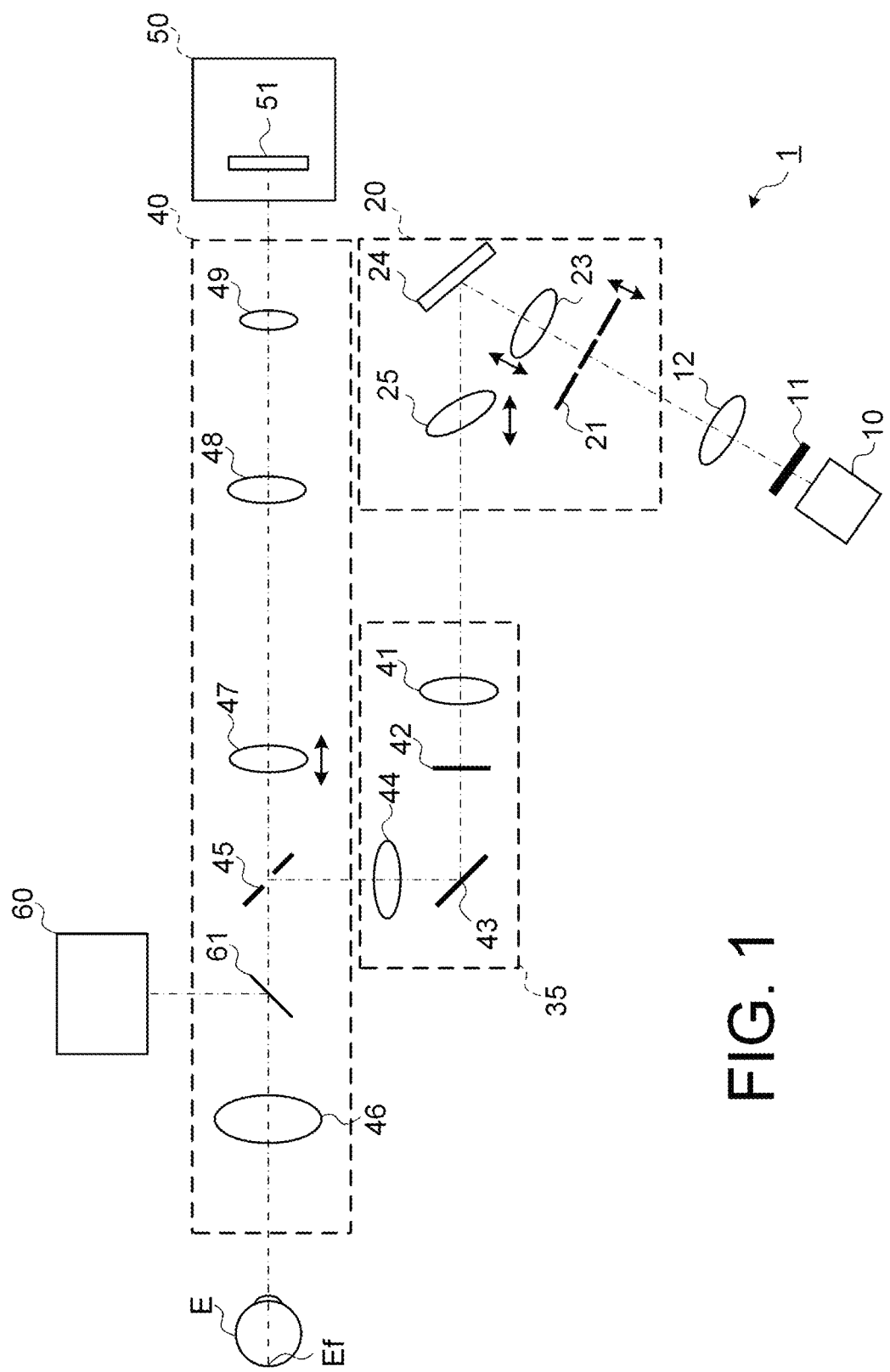
FIG. 1 is a schematic diagram illustrating an example of a configuration of an optical system of an ophthalmic apparatus according to a first embodiment.

According to the ophthalmic apparatuses disclosed in U.S. Pat. Nos. 7,831,106 and 8,237,835, a fundus can be photographed at high speed with a simple configuration. Moreover, by changing the illumination region of the illumination light on the fundus, the imaging range of the fundus can be changed as desired. However, when the illumination region is simply changed, the total light amount of illumination light on the fundus will decrease. Therefore, there is room for improvement in the illumination of the fundus.

According to some embodiments of the present invention, a new technique for acquiring a high quality image of a subject's eye with a simple configuration can be provided.

Referring now to the drawings, exemplary embodiments of an ophthalmic apparatus, a method of controlling the same, and a program according to the present invention are described below. The contents of the document cited in the present specification can be appropriately incorporated as contents of the following embodiments.

An ophthalmic apparatus according to embodiments illuminates an imaging site (predetermined site) of a subject's eye while moving an irradiated position (illumination region) of slit-shaped illumination light, and sequentially receives returning light from the imaging site using an image sensor with a one-dimensional or two-dimensional array of light receiving elements. Light receiving result(s) of the returning light is/are captured from the light receiving element(s) at light receiving position(s) (illumination range) of the returning light corresponding to the irradiated position(s) of the illumination light, in synchronization with the movement timing of the irradiated position(s) of the illumination light. For example, the light receiving result(s) of the returning light is/are acquired using a rolling shutter method. In some embodiments, slit-shaped illumination light is generated by modulating light from a light source, using a light modulator (spatial light modulator). Examples of the light modulator include a DMD (Digital Micromirror Device), a device using a reflective or transmissive liquid crystal panel, and an optical scanner. In some embodiments, the slit-shaped illumination light is generated by deflecting the light from the light source, using the optical scanner. According to such an configuration, the imaging site of the subject's eye can be imaged at high speed and the high quality image of the subject's eye can be acquired, with a simple configuration.

The ophthalmic apparatus can change the imaging region of a predetermined site by changing a size (for example, slit width or slit length (length in a direction intersecting a width direction)) of the illumination region of the illumination light on the imaging site of the subject's eye. In this case, the ophthalmic apparatus illuminates the illumination region with the illumination light having a light intensity corresponding to the size of the illumination region of the illumination light at the imaging site. For example, the ophthalmic apparatus changes the light intensity of the illumination light so that an irradiance on an anterior segment of the subject's eye remains constant. Thereby, the light intensity of the returning light from the predetermined site becomes higher, and the signal-to-noise ratio (SNR) of the light receiving result(s) of the returning light can be improved. This allows for higher quality images to be formed based on the light receiving result(s) of the returning light. As a result, it enables to observe sites of interest such as disease regions, characteristic regions in detail, and to acquire images necessary for highly accurate tracking.

In some embodiments, the predetermined site is the anterior segment or a posterior segment. Examples of the anterior segment include a cornea, an iris, a crystalline lens, a ciliary body, and a ciliary zonule. Examples of the posterior segment include a vitreous body, and a fundus or the vicinity of the fundus (retina, choroid, sclera, etc.).

A method of controlling the ophthalmic apparatus according to the embodiments includes one or more steps for realizing the processing executed by a processor (computer) in the ophthalmic apparatus according to the embodiments. A program according to the embodiments causes the processor to execute each step of the method of controlling the ophthalmic apparatus according to the embodiments. A recording medium according to the embodiments is a non-transitory recording medium (storage medium) on which the program according to the embodiments is recorded.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

Hereinafter, a case where the ophthalmic apparatus according to the embodiments photographs the fundus of the subject's eye mainly will be described.

First Embodiment

[Configuration of Optical System]

FIG. 1 illustrates an example of a configuration of an optical system of the ophthalmic apparatus according to a first embodiment. The ophthalmic apparatus 1 according to the first embodiment generates the illumination light using a DMD as the light modulator.

The ophthalmic apparatus 1 includes a light source 10, an illumination optical system 20, a projection optical system 35, an imaging optical system 40, and an imaging device 50. It should be noted that a variable neutral density filter 11 and a condenser lens 12 are arranged between the light source 10 and the illumination optical system 20, in FIG. 1. The light source 10 or the illumination optical system 20 may include the variable neutral density filter 11 and the condenser lens 12. In some embodiments, the illumination optical system 20 includes at least one of the light source 10 and the projection optical system 35. In some embodiments, the imaging optical system 40 includes the imaging device 50.

Further, the ophthalmic apparatus 1 is provided with an OCT (Optical Coherence Tomography) optical system 60 as a measurement optical system. In FIG. 1, an optical path of the OCT optical system 60 is coaxially coupled with the optical path of the imaging optical system 40 by a dichroic mirror 61 placed between an objective lens 46 and a perforated mirror 45 that are described below.

(Light Source 10)

The light source 10 includes a light source that generates light in the wavelength region including the visible region and the infrared region. For example, the light source 10 generates light with a central wavelength in the wavelength range of 420 nm to 900 nm. This type of light source 10 includes, for example, an LED (Light Emitting Diode), an LD (Laser Diode), a halogen lamp, or a xenon lamp. In some embodiments, the light source 10 includes a white light source or a light source capable of outputting light with each color component of RGB. In some embodiments, the light source 10 includes a light source capable of switching to output the light in infrared region or the light in visible region. The light source 10 is arranged at a position non-conjugate optically to each of a fundus Ef and the iris.

The variable neutral density (ND) filter 11 is a filter that varies the amount of light reduction (amount of attenuation, decrement) of the light from the light source 10. In some embodiments, the variable neutral density filter 11 selectively places two or more neutral density filters with different amounts of light reduction in an optical path of the light from the light source 10, using a known rotation mechanism or a or a slide mechanism. In some embodiments, the variable neutral density filter 11 includes two polarization filters that can change their relative angles. For example, the variable neutral density filter 11 changes the amount of light reduction of the light from the light source 10, under the control from a controller described below.

(Illumination Optical System 20)

The illumination optical system 20 generates slit-shaped illumination light using the light from the light source 10 (in FIG. 1, light passing through the variable neutral density filter 11 and the condenser lens 12). The illumination optical system 20 guides the generated illumination light to the projection optical system 35.

The illumination optical system 20 includes an iris aperture 21, a relay lens 23, a DMD 24, and a relay lens 25. The light from the light source 10 passes through an aperture formed in the iris aperture 21, is transmitted through the relay lens 23, is modulated by the DMD 24 to be guided to the relay lens 25 as the slit-shaped illumination light. The illumination light transmitted through the relay lens 25 is guided to the projection optical system 35.

(Iris Aperture 21)

The iris aperture 21 (specifically, aperture(s) described below) can be arranged at a position substantially conjugate optically to the iris (pupil) of the subject's eye E. In the iris aperture 21, one or more apertures are formed so that a luminous flux cross section of the illumination light (illumination luminous flux cross section) and a luminous flux cross section of returning light from the subject's eye E (fundus Ef) (imaging luminous flux cross section) are separated on a reflective site in the path of the illumination light in the subject's eye E. The shape of the aperture(s) formed in the iris aperture is not limited, as long as the illumination luminous flux cross section and the imaging luminous flux cross section are separated at the reflective site described above. Examples of the reflective site include a cornea (anterior surface of cornea, posterior surface of cornea), an anterior surface of lens, and a posterior surface of lens.

Specifically, in the iris aperture 21, one or more apertures are formed at positions away from the optical axis O.

Figure 2:
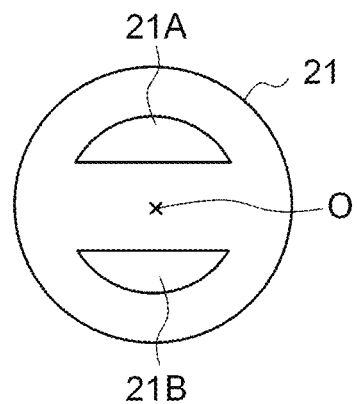
FIG. 2 is a schematic diagram illustrating an example of the configuration of the optical system of the ophthalmic apparatus according to the first embodiment.

FIG. 2 shows an example of the configuration of the iris aperture 21 when viewed from the optical axis O of the illumination optical system 20.

In the iris aperture 21, one or more apertures (in FIG. 2, apertures 21A and 21B) are formed. The aperture formed in the iris aperture 21 defines an incident position (incident shape) of the illumination light on the iris of the subject's eye E. For example, by forming the apertures 21A, 21B as shown in FIG. 2, the illumination light can enter into the eye from positions deviated from the pupil center (specifically, line symmetry to the slit direction through the pupil center) when the pupil center of the subject's eye E is arranged on the optical axis O.

That is, the apertures 21A and 21B are formed line-symmetrically with respect to a straight line extending through the position on the optical axis O in a direction corresponding to a longitudinal direction of the image (slit image) on the pupil (iris) of the slit light (slit-shaped illumination light formed by the DMD 24). The shape of the inner diameter of apertures 21A and 21B are defined by a straight line connecting two points on the inner diameter of apertures 21A and 21B so that the distance in the direction corresponding to the shorter direction of the slit image does not change.

In other words, each of the apertures 21A and 21B has a circular segment shape. The circular segment is the region bounded by the inferior arc of a circle or ellipse and the chord of this inferior arc. A direction of the chord of the circular segment shape is approximately parallel to a direction corresponding to the longitudinal direction of the slit image.

Figure 3:
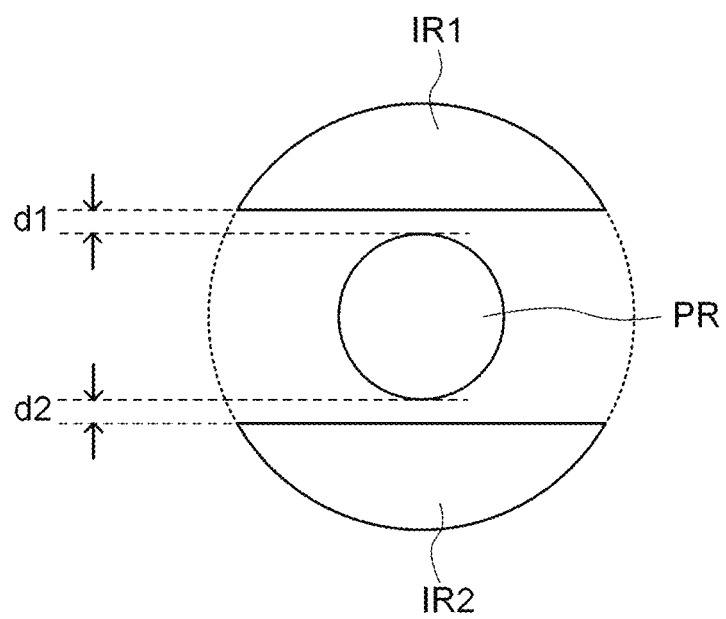
FIG. 3 is an explanatory diagram of an example of the configuration of the optical system of the ophthalmic apparatus according to the first embodiment.

FIG. 3 schematically shows an example of the luminous flux cross section on the pupil of the subject's eye E in case of illuminating the subject's eye E using the iris aperture 21.

Light passing through the apertures 21A and 21B formed in the iris aperture 21 enters into the eye so as to form the luminous flux cross sections IR1 and IR2 on the pupil, for example. The luminous flux cross section IR1 is a luminous flux cross section of the light passing through the aperture 21A, for example. The luminous flux cross section IR2 is a luminous flux cross section of the light passing through the aperture 21B, for example.

The returning light (imaging light) that enters into the eye and is reflected on the fundus Ef forms the luminous flux cross section PR on the pupil, for example, and is guided to the imaging optical system 40.

In this case, the apertures 21A and 21B are formed so as to separate the luminous flux cross sections IR1 and IR2 of the illumination light and the luminous flux cross section PR of the imaging light.

Figure 4:
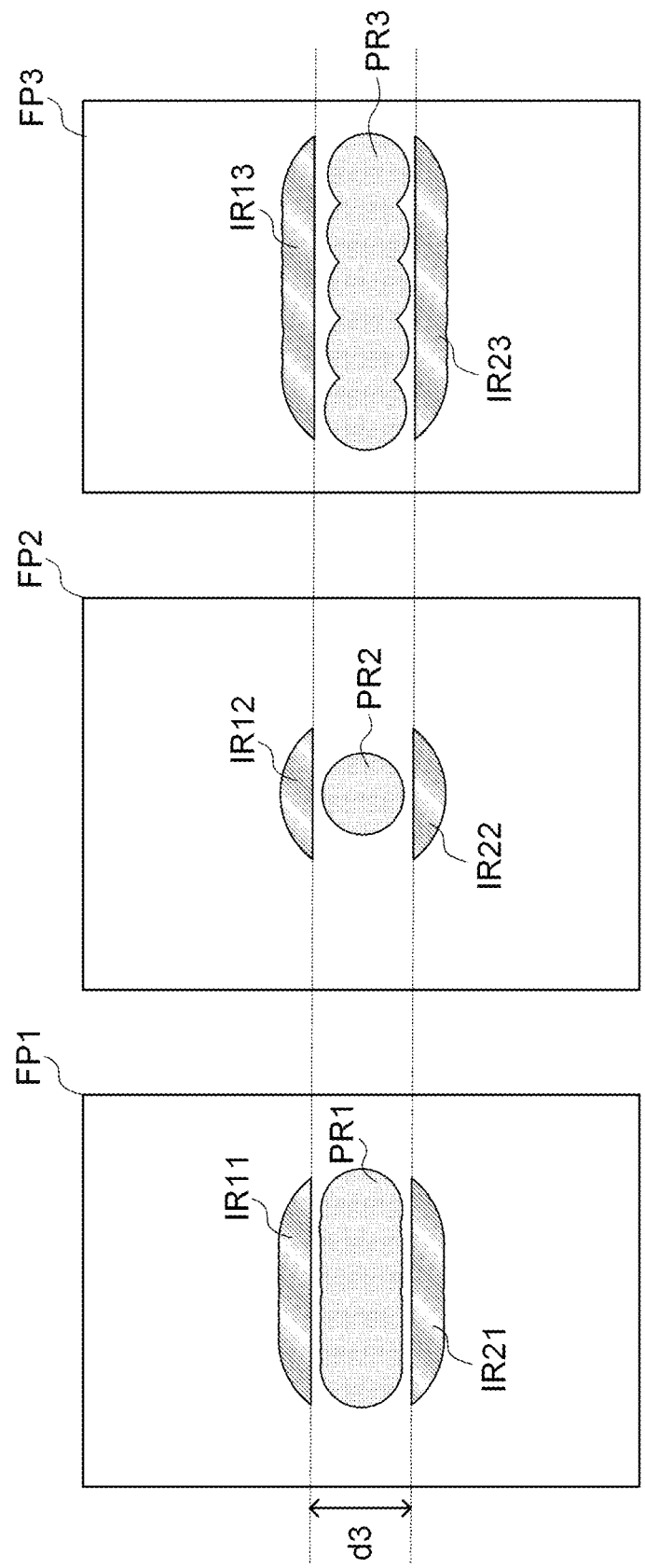
FIG. 4 is an explanatory diagram of an example of the configuration of the optical system of the ophthalmic apparatus according to the first embodiment.

FIG. 4 schematically shows the illumination luminous flux cross section and the imaging luminous flux cross section at each part in the eye of the subject's eye E in case of illuminating the subject's eye E using the iris aperture 21. FIG. 4 schematically represents footprints FP1 to FP3 when the slit light illuminating a predetermined illumination region is formed by the DMD 24 described below. The footprint FP1 represents the luminous flux cross section on the surface of the cornea. The footprint FP2 represents the luminous flux cross section on the anterior surface of lens (surface of the iris) (or surface of the photographic stop). The footprint FP3 represents the luminous flux cross section on the posterior surface of lens.

The anterior surface of lens (iris surface) (or surface of the photographic stop) is a position substantially conjugate optically to the iris aperture 21. Thereby, as shown in the footprint FP2, the same illumination luminous flux cross sections IR12 and IR22 and the imaging luminous flux cross section PR2 as in FIG. 3 are formed. The respective shapes of the illumination luminous flux cross sections IR12 and IR22 are almost the same as the respective shapes of the apertures 21A and 21B formed in the iris aperture 21. The shape of the imaging luminous flux cross section PR2 is almost the same as the shape of the photographic stop (aperture formed in the perforated mirror 45). At the position substantially conjugate optically to the iris aperture 21, the illumination luminous flux cross section and the imaging luminous flux cross section are separated, as in the footprint FP2.

On the corneal surface, which is non-conjugate optically to the iris aperture 21, the illumination luminous flux cross sections IR11 and IR21 and the imaging luminous flux cross section PR1 spread in the direction corresponding to the longitudinal direction of the slit image (footprint FP1). Meanwhile, the relative relationship between the illumination luminous flux cross sections IR11 and IR21 and the imaging luminous flux cross section PR1 in the direction corresponding to the shorter direction of the slit image does not change.

In the same way, on the posterior surface of lens, which is non-conjugate optically to the iris aperture 21, the illumination luminous flux cross sections IR13 and IR23 and the imaging luminous flux cross section PR3 spread in the direction corresponding to the longitudinal direction of the slit image (footprint FP3). Meanwhile, the relative relationship between the illumination luminous flux cross sections IR13 and IR23 and the imaging luminous flux cross section PR3 in the direction corresponding to the shorter direction of the slit image does not change.

At the position non-conjugate optically to the iris aperture 21, when the slit position is changed by the DMD 24 described below, the positions of the illumination luminous flux cross section and the imaging luminous flux cross section move in the direction corresponding to the shorter direction of the slit image. Even if the position of the illumination region of the slit light is changed, the relative relationship between the illumination luminous flux cross section and the imaging luminous flux cross section as shown in footprints FP1 and FP3 is maintained.

Therefore, the aperture 21A formed in the iris aperture 21 is required to be formed so that the distance d1 (distance in the direction corresponding to the shorter direction of the slit image) between the lower end of the illumination luminous flux cross section (luminous flux cross section IR1) and the upper end of the imaging luminous flux cross section (luminous flux cross section PR) is greater than or equal to a predetermined first distance, as shown in FIG. 3. In the same way, the aperture 21B formed in the iris aperture 21 is required to be formed so that the distance d2 between the upper end of the illumination luminous flux cross section (luminous flux cross section IR2) and the lower end of the imaging luminous flux cross section (luminous flux cross section PR) is greater than or equal to a predetermined second distance, as shown in FIG. 3. Here, the first distance may be equal to the second distance. Further, the apertures 21A and 21B formed in the iris aperture 21 are required to be formed so that the distance d3 in the direction corresponding to the shorter direction of the slit image is greater than or equal to a predetermined third distance, as shown in FIG. 3.

That is, the shapes of the inner diameters of the apertures 21A and 21B does not contribute to the shapes of the illumination luminous flux cross section and the shape of the imaging luminous flux cross section.

As described above, the apertures 21A and 21B are formed in the iris aperture 21 so that the illumination luminous flux cross section and the imaging luminous flux cross section are separated at the cornea, the anterior surface of lens, and the posterior surface of lens of the subject's eye E. Thereby, without being affected by unnecessary scattered light, high quality images of the fundus Ef with strong contrast can be acquired using a simple configuration.

In particular, by shaping the apertures 21A and 21B as shown in FIG. 2, the light amount of the illumination light can be increased, making it possible to acquire images with higher image quality.

In some embodiments, in the iris aperture 21, the aperture having a predetermined thickness along a circumferential direction centered with the optical axis O is formed.

(DMD 24)

The DMD 24 can be arranged at a position substantially conjugate optically to the fundus Ef (imaging site) of the subject's eye E. The DMD 24 includes a plurality of micromirror devices arranged in a two-dimensional array on an irradiation surface where the light transmitted through the relay lens 23 is irradiated. The deflection surface of each micromirror device is controlled by the controller described below. Thereby, the light transmitted through the relay lens 23 can be modulated. Therefore, by controlling the deflection surface of each micromirror device, the light transmitted through the relay lens 23 can be guided to the irradiation region having a desired shape set at any position of the fundus Ef.

(Relay Lens 25)

The relay lens 25 is a tilted lens. Further, the relay lens 25 may include one or more lenses. The relay lens 25 can be moved along an optical axis of the illumination optical system 20 (the optical path of the illumination light modulated by the DMD 24). For example, the ophthalmic apparatus 1 includes a known movement mechanism that moves the relay lens 25 along the optical axis of the illumination optical system 20, and the controller described below controls the movement mechanism to move the relay lens 25 in accordance with a dioptric power (in a broad sense, the shape of the fundus Ef) of the subject's eye E. This allows to arrange the DMD 24 at a position substantially conjugate optically to the fundus Ef, regardless of the dioptric power the subject's eye E.

Further, the relay lens 25, relay lenses 41 and 44, and the objective lens 46 constitute a Badal optical system according to Badal's principle. This allows to keep the size of the slit image at the fundus Ef constant, regardless the dioptric power of the subject's eye E.

Figure 5:
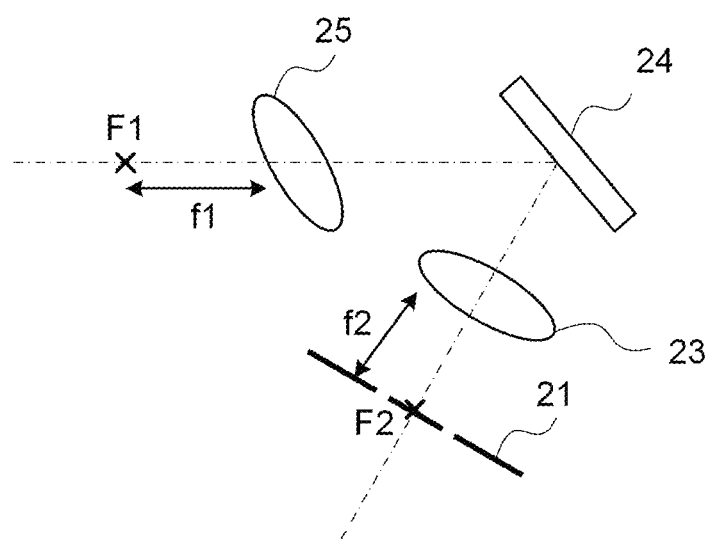
FIG. 5 is an explanatory diagram of an example of the configuration of the optical system of the ophthalmic apparatus according to the first embodiment.

FIG. 5 illustrates an example of the configuration of the illumination optical system 20 according to the first embodiment. In FIG. 5, parts similar to those in FIG. 1 are denoted by the same reference symbols, and description thereof is omitted as appropriate.

A back focal position F1 of the relay lens 25 is arranged at a position substantially conjugate optically to the iris of the subject's eye E. Therefore, the size of the slit image (image formed by the slit light) projected onto the fundus Ef does not change, regardless the dioptric power of the subject's eye E. That is, the projected angle of view (projection magnification) of the slit image with reference to the visual axis of the subject's eye E (longitudinal and shorter directions of the slit image) can be kept constant, regardless the dioptric power of the subject's eye E. As a result, the size of the slit image does not change regardless of the dioptric power of the subject's eye E. This allows to simplify the control for the DMD 24.

In addition, since the projected angle of view (projection magnification) of the slit image with reference to the visual axis of the subject's eye E is constant regardless of the dioptric power of the subject's eye E, the illumination intensity of the slit image at the fundus Ef can be kept constant regardless of the dioptric power of the subject's eye E.

(Relay Lens 23)

The relay lens 23 includes one or more lenses. The relay lens 23 can be moved along the optical axis of the illumination optical system 20. For example, the ophthalmic apparatus 1 includes a known movement mechanism that moves the relay lens 23 along the optical axis of the illumination optical system 20, and the controller described below controls the movement mechanism to move the relay lens 23 in accordance with a dioptric power of the subject's eye E.

As described above, the relay lens 25 is moved according to the dioptric power of the subject's eye E. As a result, the position of the iris aperture 21 is shifted from the position substantially conjugate optically to the iris of the subject's eye E. In this case, by moving the relay lens 23, even if the relay lens 25 is moved, the position of the iris aperture 21 can be placed at a position substantially conjugate optically to the iris of the subject's eye E.

In some embodiments, the iris aperture 21 can be moved along the optical path of the illumination optical system 20. This allows to place the iris aperture 21 at a position substantially conjugate optically to the iris of the subject's eye E even when the relay lens 25 is moved.

As shown in FIG. 5, the iris aperture 21 is arranged at a front focal position F2 of the relay lens 25 or the vicinity of the front focal position F2.

That is, the back focal position F1 of the relay lens 23 is the position substantially conjugate optically to the iris aperture 21, and the iris aperture 21 is arranged at the front focal position F2 of the relay lens 25. Therefore, the projection magnification from the iris aperture 21 to the back focal position F1 is determined by a focal distance f1 of the relay lens 23 and a focal distance f2 of the relay lens 25. In this case, the projection magnification is (f1/f2).

The ophthalmic apparatus according to the embodiments is required to form images of the iris aperture 21 with a predetermined size on the iris of the subject's eye E. When the projection magnification from the iris of the subject's eye E to the back focal position F1 via the objective lens 46 is a known projection magnification, an image of the iris aperture 21 with a predetermined size should be projected at a position substantially conjugate optically to the iris. In this case, the projection magnification from the iris aperture 21 to the back focal position F1 is determined by the focal distance f of the relay lens 23 and the focal distance f2 of the relay lens 25. Therefore, by changing at least one of the focal distances f1 and f2, the image of the iris aperture 21 can be easily formed on the iris of the subject's eye E with a predetermined size. In some embodiments, while the focal distance f1 remains fixed, the focal distance f2 is changed alone.

The focal distance f1 is a composite focal distance of the relay lens 25. In some embodiments, the relay lens 25 includes a plurality of the lenses with different dioptric powers, and changes the focal distance f1 by changing at least one of the lenses constituting the relay lens 25. In some embodiments, at least one of the lenses constituting the relay lens 25 is a lens whose dioptric power can be changed. Examples of the lens whose dioptric power can be changed include a liquid crystal lens, a liquid lens, and an Alvarez lens. Even when the focal distance f1 is changed, the back focal position of the relay lens 25 is arranged at a position substantially conjugate optically to the iris (pupil conjugate position) of the subject's eye E.

The focal distance 2 is a composite focal distance of the relay lens 23. In some embodiments, the relay lens 23 includes a plurality of the lenses with different dioptric powers, and changes the focal distance f2 by changing at least one of the lenses constituting the relay lens 23. In some embodiments, at least one of the lenses constituting the relay lens 23 is a lens whose dioptric power can be changed. Even when the focal distance f2 is changed, the front focal position of the relay lens 23 is arranged at a position substantially conjugate optically to the iris (pupil conjugate position) of the subject's eye E.

In addition, for imaging the fundus Ef, it is desirable to use a light source that emits a high-intensity light. However, light sources available for general use (light sources that are mass-produced) are limited in the size of the emitting surface (luminous area, output luminous flux cross section size). Thereby, the image of the iris aperture 21 should be projected at the back focal position F1 with a projection magnification corresponding to the size of the emitting surface of the light source.

According to the present embodiment, by changing at least one of the focal distances f1 and f2, the projection magnification from the iris aperture 21 to the back focal position F1 can be changed. Thereby, the image of the iris aperture 21 with any size can be projected at the back focal position F1 with a desired size. This allows to project the image of the iris aperture 21 with the desired size at the to the back focal position F1 by simply changing at least one of the focal distances f1 and f2 even when the size of the emitting surface of the light source is different and to improve the degree of freedom in designing optical systems. In particular, this allows to fix the movement amount of the relay lens 25 in response to changes in the dioptric power of the subject's eye E (sensitivity of the movement of the relay lens 25 in response to changes in the dioptric power) by fixing the focal distance f1 and changing the focal distance f2 alone. Therefore, the degree of freedom in designing optical systems can be further improved.

(Projection Optical System 35)

The projection optical system 35 guides the illumination light formed by the illumination optical system 20 to the fundus Ef of the subject's eye E. In the embodiments, the projection optical system 35 guides the illumination light to the fundus Ef through an optical path coupled with the optical path of the imaging optical system 40 by the perforated mirror 45 as the optical path coupling member described below.

The projection optical system 35 includes the relay lens 41, a black point plate 42, a reflective mirror 43, and a relay lens 44. Each of the relay lenses 41 and 44 includes one or more lenses.

(Black Point Plate 42)

The black point plate 42 is arranged at a position substantially conjugate optically to a lens surface of the objective lens 46 or the vicinity of the lens surface of the objective lens 46. This prevents the reflected light from the lens surface of the objective lens 46 from being guided to the light source 10.

In the projection optical system 35 with this configuration, the illumination light generated by the illumination optical system 20 is transmitted through the relay lens 41, passes through the black point plate 42, is reflected by the reflective mirror 43 toward the perforated mirror 45.

(Imaging Optical System 40)

The imaging optical system 40 guides the illumination light that has been guided through the projection optical system 35 to the fundus Ef of the subject's eye E, and also guides the returning light of the illumination light from the fundus Ef to the imaging device 50.

In the imaging optical system 40, an optical path of the illumination light from the projection optical system 35 and an optical path of the returning light of the illumination light from the fundus Ef are coupled. By using the perforated mirror 45 as an optical path coupling member to couple these optical paths, it enables pupil division between the illumination light and the returning light of the illumination light.

The imaging optical system 40 includes the perforated mirror 45, the objective lens 46, a focusing lens 47, a relay lens 48, and an imaging lens 49. Each of relay lens 48 includes one or more lenses. In FIG. 1, the imaging optical system 40 includes the dichroic mirror 61 described above.

(Perforated Mirror 45)

In the perforated mirror 45, the hole is formed. The hole is arranged on the optical axis of the imaging optical system 40. The hole in the perforated mirror 45 is arranged at a position substantially conjugate optically to the ins of the subject's eye E. The perforated mirror 45 reflects the illumination light from the projection optical system 35 toward the objective lens 46, on the peripheral region of the hole. The perforated mirror 45 with this configuration functions as a photographic stop.

That is, the perforated mirror 45 is configured to combine the optical path of the illumination optical system 20 (projection optical system 35) and the optical path of the imaging optical system 40 arranged in a direction of the optical axis passing through the hole, and also to guide the illumination light reflected on the peripheral region of the hole to the fundus Ef.

It should be noted that in FIG. 1, the optical axis of the imaging optical system 40 passes through the hole formed in the perforated mirror 45, and the projection optical system 35 (illumination optical system 20) is placed in the reflection direction of the perforated mirror 45. However, the configuration according to the embodiments is not limited to this. For example, the optical axis of the projection optical system 35 (illumination optical system 20) may pass through the hole formed in the perforated mirror 45, and the imaging optical system 40 may be placed in the reflection direction of the perforated mirror 45.

(Focusing Lens 47)

The focusing lens 47 can be moved in an optical axis direction of the imaging optical system 40 using a movement mechanism (not shown). The movement mechanism moves the focusing lens 47 in the optical axis direction under the control from the controller 100 described below. This allows to image the returning light of the illumination light passing through the hole of the perforated mirror 45 on the light receiving surface of the image sensor 51 in the imaging device 50 in accordance with the state of the subject's eye E.

In the imaging optical system 40 with this configuration, the illumination light from the projection optical system 35 is reflected toward the objective lens 46 on the peripheral region of the hole formed in the perforated mirror 45. The illumination light reflected on the peripheral region of perforated mirror 45 is refracted by the objective lens 46, enters into the eye through the pupil of the subject's eye E, and illuminates the fundus Ef of the subject's eye E.

The returning light of the illumination light from the fundus Ef is refracted by the objective lens 46, passes through the hole of the perforated mirror 45, is transmitted through the focusing lens 47, is transmitted through the relay lens 48, is imaged on the light receiving surface of the image sensor 51 in the imaging device 50 through the imaging lens 49.

(Imaging Device 50)

The imaging device 50 includes the image sensor 51 receiving the returning light of the illumination light that has been guided from the fundus Ef of the subject's eye E through the imaging optical system 40. The imaging device 50 can perform readout control of the light receiving result of the returning light under the control from the controller (10) described below.

(Image Sensor 51)

The image sensor 51 realizes the function as a pixelated photodetector. The light receiving surface (detecting surface, imaging surface) of the image sensor 51 can be arranged at a position substantially conjugate optically to the fundus Ef.

The light receiving result(s) obtained using the image sensor 51 is read out using a rolling shutter method under the control from the controller 100 described below.

The image sensor 51 with this configuration includes the CMOS image sensor. In this case, the image sensor 51 includes a plurality of pixels (light receiving elements) arranged in a plurality of pixel groups in a column direction, the pixel groups being arranged in a row direction. Specifically, the image sensor 51 includes a plurality of pixels, a plurality of vertical signal lines, and a horizontal signal line. Each pixel includes a photodiode (light receiving element), and a capacitor. The vertical signal line is provided for each pixel group in the column direction (vertical direction) orthogonal to the row direction (horizontal direction). Each of the vertical signal lines is selectively electrically connected to the pixel group in which the electrical charge corresponding to the light receiving result is accumulated. The horizontal signal line is selectively electrically connected to the vertical signal lines. Each of the pixels accumulates the electrical charge corresponding to the light receiving result of the returning light. The accumulated electrical charge is read out sequentially for each pixel group in the row direction, for example. For example, for each line in the row direction, a voltage corresponding to the electrical charge accumulated in each pixel is supplied to the vertical signal line. The vertical signal lines are selectively electrically connected to the horizontal signal line. By performing readout operation for each line in the row direction described above sequentially in the vertical direction, the light receiving results of the plurality of pixels arranged two-dimensionally can be read out.

By capturing (reading out) the light receiving results of the returning light using the rolling shutter method for this type of image sensor 51, the light receiving image corresponding to the desired virtual aperture shape extending in the row direction is acquired. Such control is disclosed in, for example, U.S. Pat. No. 8,237,835.

Figure 6:
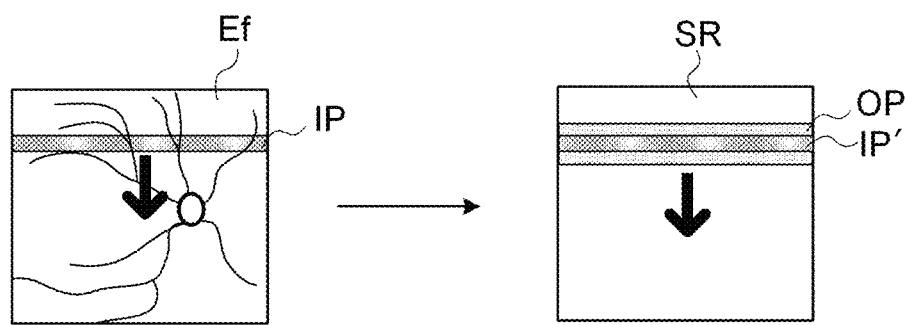
FIG. 6 is an explanatory diagram of an operation of the ophthalmic apparatus according to the first embodiment.

FIG. 6 shows a diagram explaining the operation of the ophthalmic apparatus 1 according to the embodiments. FIG. 6 schematically represents an illumination region IP of the slit-shaped illumination light irradiated on the fundus Ef and a virtual opening range OP on the light receiving surface SR of the image sensor 51.

For example, the controller 100 described below can control the DMD 24 to illuminate the illumination light onto the illumination region with the desired shape at any position within a predetermined imaging region on the fundus Ef. Thereby, the illumination region IP of the slit-shaped illumination light can be sequentially moved in a direction (for example, the vertical direction) orthogonal to the slit direction (for example, the row direction, the horizontal direction) on the fundus Ef.

On the light receiving surface SR of the image sensor 51, by changing the pixels to be read out in units of lines by the controller 100 described below, the virtual opening range OP is set. The opening range OP is preferable to be the light receiving range IP' of the returning light of the illumination light on the light receiving surface SR or wider than the light receiving range IP'. The controller 100 described below performs the movement control of the opening range OP in synchronization with the movement control of the illumination region IP of the illumination light on the fundus Ef. Thereby, without being affected by unnecessary scattered light, high quality images of the fundus Ef with strong contrast can be acquired using a simple configuration.

Figure 7:
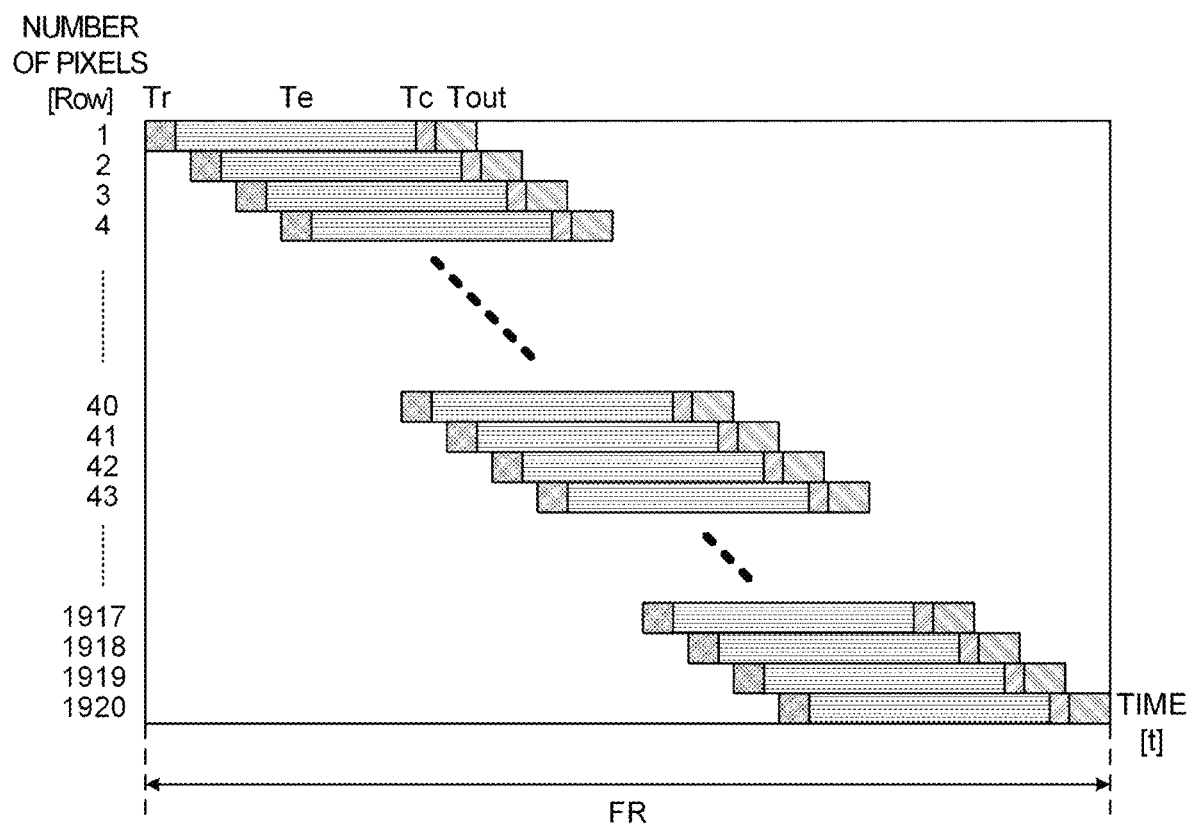
FIG. 7 is an explanatory diagram of an operation of the ophthalmic apparatus according to the first embodiment.
Figure 8:
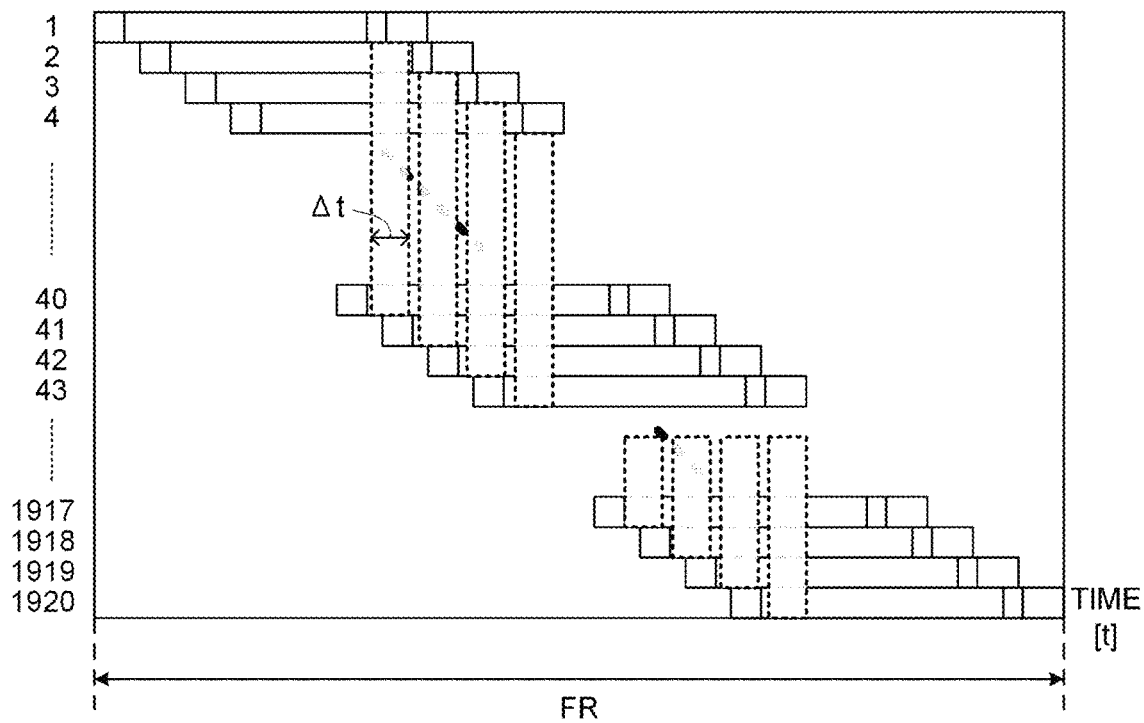
FIG. 8 is an explanatory diagram of an operation of the ophthalmic apparatus according to the first embodiment.

FIGS. 7 and 8 schematically show examples of the control timing of the rolling shutter method for the image sensor 5. FIG. 7 represents an example of the timing of the readout control for the image sensor 51. FIG. 8 represents the timing of the movement control for the illumination region IP (the light receiving range IP' on the light receiving surface SR) of the illumination light on the fundus Ef superimposed on the timing of the readout control in FIG. 7. In FIGS. 7 and 8, the horizontal axis represents the number of rows in the image sensor 51, and the vertical axis represents time.

In addition, in FIGS. 7 and 8, for convenience of explanation, it is assumed that the number of rows in the image sensor 51 is 1920. However, the configuration according to the embodiments is not limited to the number of rows. Further, in FIG. 8, for convenience of explanation, it is assumed that the slit width (width in the row direction) of the slit-shaped illumination light is 40 rows.

The readout control in the row direction includes the reset control, the exposure control, the charge transfer control, and the output control. The reset control is a control that initializes the amount of electrical charge accumulated in the pixels in the row direction. The exposure control is a control that illuminates light on the photodiode and accumulates the electrical charge corresponding to the amount of received light in the capacitor. The charge transfer control is a control that transfers the amount of the electrical charge accumulated in the pixel to the vertical signal line. The output control is a control that outputs the amount of the electrical charge accumulated in the plurality of vertical signal lines via the horizontal signal line. That is, as shown in FIG. 7, the readout time T for reading out the electrical charge accumulated in the pixels in the row direction is the sum of the time Tr required for the reset control, the time Te required for the exposure control (exposure time), the time Tc required for the charge transfer control, and the time Tour required for the output control.

In FIG. 7, by shilling the readout start timing (start timing of time Tc) in units of rows, the light receiving results (amount of electrical charge) accumulated in the pixels in the desired range in the image sensor 51 are acquired. For example, in case that the pixel range shown in FIG. 7 is for a single frame of the image, the frame rate FR is determined uniquely.

In the present embodiment, the illumination region of the illumination light on the fundus Ef, the illumination light having a slit width of a plurality of rows, is sequentially shifted in a direction corresponding to the column direction on the fundus Ef.

For example, as shown in FIG. 8, at each predetermined shift time $\Delta t$, the illumination region of the illumination light on the fundus Ef is shifted in row units in the direction corresponding to the column direction. The shift time $\Delta t$ is obtained by dividing the exposure time Te of the pixel in the image sensor 51 by the slit width of the illumination light (e.g., 40) ($\Delta t = Te/40$). Synchronized with this movement timing of the illumination region, the readout start timing of each row of pixels is delayed and is started for each row in units of shift time $\Delta t$. This allows to acquired high quality images of the fundus Ef with strong contrast in a short time with a simple control.

In some embodiments, the image sensor 51 is configured using one or more line sensors.

(OCT Optical System 60)

The OCT optical system 60 includes an interference optical system for performing OCT measurement. The interference optical system is configured to split light from an OCT light source into reference light and measurement light, to irradiate the measurement light onto the subject's eye, and to detect interference light between the reference light traveling through a reference optical path and returning light of the measurement light from the subject's eye, and to detect the generated interference light. Here, the measurement light is guided to the objective lens 46 via the dichroic mirror 61, is refracted by the objective lens 46 to be irradiated onto the subject's eye E (for example, the fundus EQ. The measurement light is scattered (and reflected) at various depth positions of the subject's eye E. The backscattered light of the measurement light generated by the subject's eye E advances in the same path as the forward path in the opposite direction and is led to the OCT optical system 60 as the returning light of the measurement light. The OCT optical system 6i0 may be a known optical system for performing a swept source type OCT, a spectral domain type OCT, or a time domain type OCT.

The dichroic mirror 61 reflects light in the wavelength range with the wavelength component used for the OCT measurement as the center wavelength, and transmits through light in the wavelength range with the wavelength component of the illumination light illuminated by the illumination optical system 20.

It should be noted that in FIG. 1, a case where the measurement optical system is the OCT optical system 60 will be described. However, the measurement optical system provided in the ophthalmic apparatus according to the embodiments is not limited to the optical system having an OCT function. For example, the measurement optical system such as an eye refractive power measurement function, an axial length measurement function, an intraocular pressure measurement function, and ultrasonography function may be provided in the ophthalmic apparatus 1. The axial length measurement function is realized by the OCT, etc. The axial length measurement function may be done to measure the axial length of the subject's eye by projecting light onto the subject's eye and detecting returning light from the fundus while adjusting the position of the optical system in the optical axis direction (front-back direction) relative to the subject's eye. The intraocular pressure measurement function is realized by the tonometer, etc. In addition, the measurement optical system having two or more functions among the above functions may also be provided in the ophthalmic apparatus 1.

The ophthalmic apparatus 1 with the configuration described above can have two or more imaging modes with different sizes of the illumination region on the fundus Ef, and can control the illumination optical system so as to illuminate the illumination region with the illumination light, the illumination region corresponding to the designated imaging mode among the two or more imaging modes.

In the first embodiment, the two or more imaging modes include fundus imaging mode and tracking mode. The fundus imaging mode is the imaging mode for acquiring a front image of a predetermined imaging region on the fundus Ef. Tracking mode is the imaging mode for acquiring the front image for performing tracking control. The imaging region (i.e., the illumination region of the illumination light) in the tracking mode is narrower than the imaging region in the fundus imaging mode.

When the fundus imaging mode is designated as the imaging mode, the illumination optical system 20 generates the slit-shaped illumination light with at least one of the length in the slit direction length and the slit width predetermined for the fundus imaging mode. This allows to illuminate the illumination region having the size predetermined for the fundus imaging mode with illumination light. Further, the image sensor 51 is controlled to set an opening range so as to overlap the illumination range of the returning light on the light receiving surface SR corresponding to the illumination region set for the fundus imaging mode, and to sequentially capture the light receiving results obtained by the light receiving elements in the set opening range.

When the tracking mode is designated as the imaging mode, the illumination optical system 20 generates the slit-shaped illumination light with at least one of the length in the slit direction length and the slit width predetermined for the tracking mode. This allows to illuminate the illumination region having the size predetermined for tracking mode with illumination light. Further, the image sensor 51 is controlled to set an opening range so as to overlap the illumination range of the returning light on the light receiving surface SR corresponding to the illumination region set for the tracking mode, and to sequentially capture the light receiving results obtained by the light receiving elements in the set opening range.

In some embodiments, the length in the slit direction in the tracking mode is shorter than the length in the slit direction in the fundus imaging mode. In some embodiments, the slit width in the tracking mode is narrower than the slit width in the fundus imaging mode. In some embodiments, the length in the slit direction in the tracking mode is shorter than the length in the slit direction in the fundus imaging mode, and the slit width in the tracking mode is narrower than the slit width in the fundus imaging mode. In some embodiments, the length in the slit direction is the same in the fundus imaging mode and the tracking mode, and the slit width in the tracking mode is narrower than the slit width in the fundus imaging mode. In some embodiments, the slit width is the same in the fundus imaging mode and the tracking mode, and the length in the slit direction in the tracking mode is shorter than the length in the slit direction in the fundus imaging mode.

And now, when the size of the illumination region of the illumination light on the fundus Ef is changed, the light amount of the illumination light reaching the fundus Ef is also changed. Therefore, the illumination optical system 20 can change the light intensity per unit time of the illumination light in accordance with the size, which is changed by designating the imaging mode, of the illumination region of the illumination light on the fundus Ef. Specifically, the illumination optical system 20 generates the illumination light so that the light intensity increases when the size of the illumination region on the fundus Ef is switched to a smaller size, and that the light intensity decreases when the size of the illumination region is switched to a larger size. In some embodiments, the illumination optical system changes the light intensity of the illumination light so that the irradiance on the anterior segment of the subject's eye E remains constant.

Figure 9A:
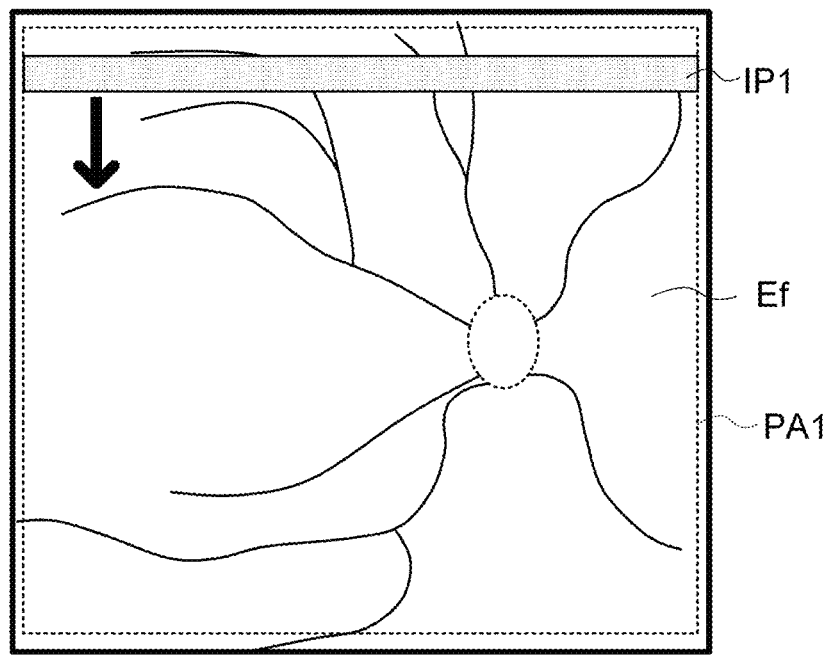
FIG. 9A is a schematic diagram for explaining the operation of the ophthalmic apparatus according to the first embodiment.
Figure 9B:
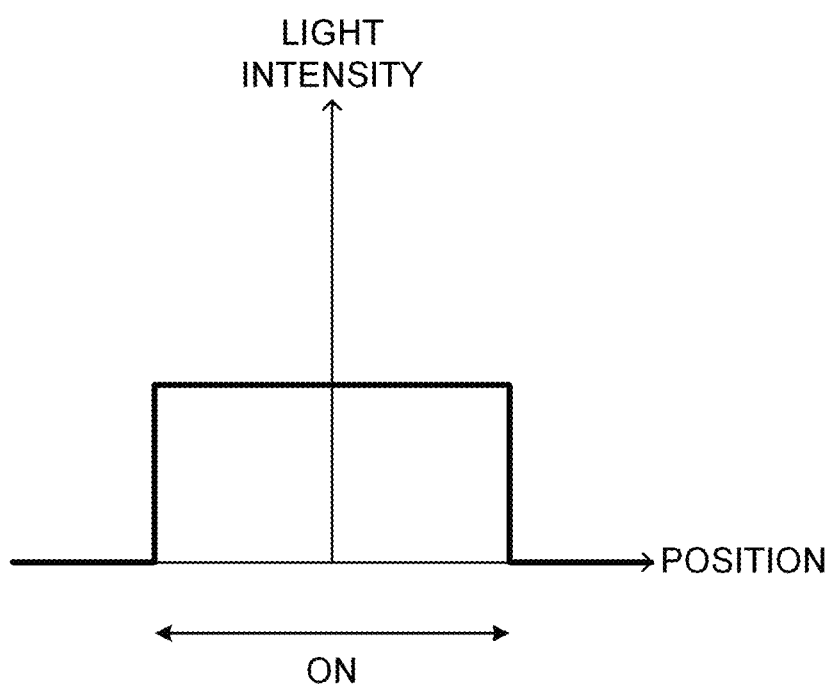
FIG. 9B is a schematic diagram for explaining the operation of the ophthalmic apparatus according to the first embodiment.

FIGS. 9A and 9B show diagrams explaining the fundus imaging mode according to the embodiments. FIG. 9A schematically represents the imaging region PA1 of the fundus Ef in the fundus imaging mode and the illumination region IP1 of the illumination light that moves on the imaging region PAL. In FIG. 9B, the horizontal axis schematically represents the position in the slit width direction on the light receiving surface of the DMD 24, and the vertical axis represents the light intensity of the illumination light (per unit time).

As described above, when the fundus imaging mode is designated, the illumination region IP1 of the illumination light is set so as to sequentially move on a predetermined imaging region PA1 of the fundus Ef corresponding to the fundus imaging mode. The illumination region IP1 moves sequentially in the direction perpendicular to the slit direction. The image sensor 51 is controlled to set an opening range so as to overlap the illumination range of the returning light on the light receiving surface SR corresponding to the illumination region IP1, and to sequentially capture the light receiving results obtained by the light receiving elements in the set opening range.

The illumination optical system 20 changes the light intensity of the illumination light in accordance with the size of the illumination region IP1, as shown in FIG. 9B. In this case, the light having the changed light intensity is reflected by the micromirror device at the on position in the slit width direction of the DMD 24, and is guided to projection optical system 35 as the slit-shaped illumination light.

Figure 10A:
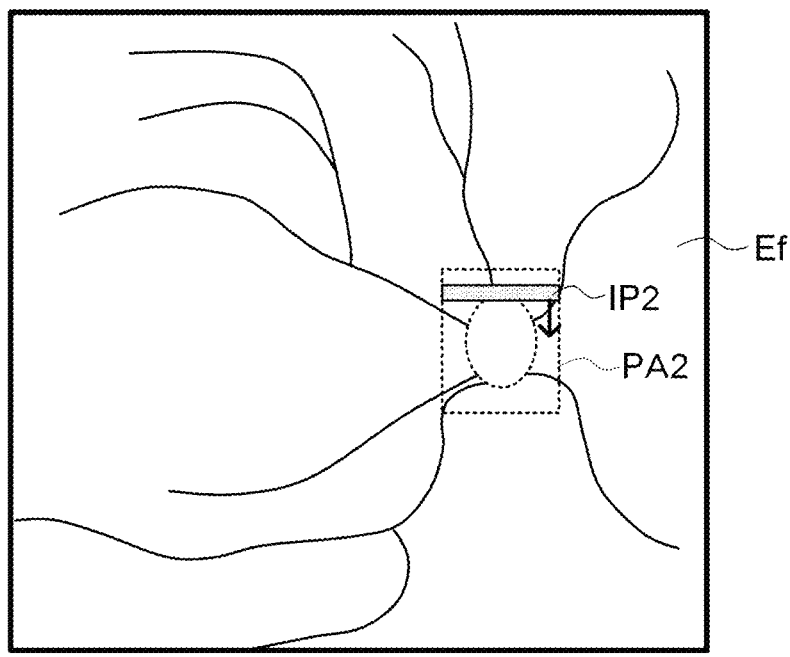
FIG. 10A is a schematic diagram for explaining the operation of the ophthalmic apparatus according to the first embodiment.
Figure 10B:
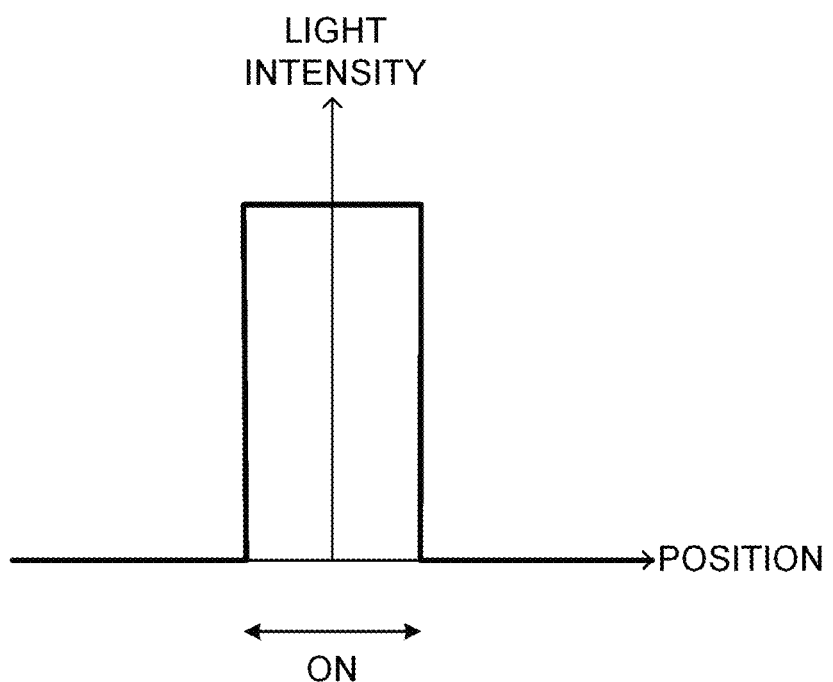
FIG. 10B is a schematic diagram for explaining the operation of the ophthalmic apparatus according to the first embodiment.

FIGS. 10A and 10B show diagrams explaining the tracking mode according to the embodiments. FIG. 10A schematically represents the imaging region PA2 of the fundus Ef in the tracking mode and the illumination region IP2 of the illumination light that moves on the imaging region PA2. In FIG. 10B, the horizontal axis schematically represents the position in the slit width direction on the light receiving surface of the DMD 24, and the vertical axis represents the light intensity of the illumination light.

As described above, when the tracking mode is designated, the illumination region IP2 of the illumination light is set so as to sequentially move on a predetermined imaging region PA2 of the fundus Ef corresponding to the tracking mode. The illumination region IP2 moves sequentially in the direction perpendicular to the slit direction. The image sensor 51 is controlled to set an opening range so as to overlap the illumination range of the returning light on the light receiving surface SR corresponding to the illumination region IP2, and to sequentially capture the light receiving results obtained by the light receiving elements in the set opening range.

In the tracking mode, the imaging region PA2 is set so as to include the site of interest on the fundus Ef. Examples of the site of interest include a characteristic site such as an optic disc, a blood vessel, a diseased region, a scar, and a site designated using the operation unit described below. In FIG. 10A, the imaging region PA2 is set so as to include the optic disc.

The illumination optical system 20 changes the light intensity of the illumination light in accordance with the size of the illumination region IP2, as shown in FIG. 10B. In this case, the light having the changed light intensity is reflected by the micromirror device at the on position in the slit width direction of the DMD 24, and is guided to projection optical system 35 as the slit-shaped illumination light.

Thereby, in the tracking mode, the light intensity of the returning light from the fundus Ef is higher than in the fundus imaging mode. This allows to improve the SNR of the light receiving results of the returning light and to enhance the image quality of the image formed based on the light receiving results of the returning light. As a result, the site of interest can be observed in detail and the images necessary for highly accurate tracking can be acquired.

In some embodiments, by controlling the light source 10 to change the light intensity of the light output from the light source 10, the light intensity of the illumination light generated by the DMD 24 is changed. In some embodiments, by controlling the variable neutral density filter 11 to change the light intensity of the light reaching the DMD 24, the light intensity of the illumination light generated by the DMD 24 is changed. In some embodiments, by controlling the light source 10 and the variable neutral density filter 11, the light intensity of the illumination light generated by the DMD 24 is changed. For example, the light source 10 is controlled to reduce the light intensity of the light output from the light source 10, and the variable neutral density filter 11 is controlled to further reduce the light intensity of the light output from the light source 10. That is, the variable neutral density filter 11 is used to compensate for the amount of light reduction of the light source 10. In an opposite way, for example, the variable neutral density filter 11 is controlled to reduce the light intensity of the light output from the light source 10, and further the light source 10 is controlled to further reduce the light intensity of the light output from the light source 10. That is, the light source 10 is used to compensate for the amount of light attenuation of the variable neutral density filter 11.

(Other Configurations)

In some embodiments, the ophthalmic apparatus 1 further includes a fixation projection system. Further, an optical path of the fixation projection system is coupled with the optical path of the imaging optical system 40 in the configuration of the optical system shown in FIG. 1. The fixation projection system can present internal fixation targets or external fixation targets to the subject's eye E. In case of presenting the internal fixation target to the subject's eye E, the fixation projection system includes an LCD that displays the internal fixation target under the control from the controller described below, and projects a fixation light flux output from the LCD onto the fundus Ef of the subject's eye E. The LCD is configured to be capable of changing the display position of the fixation target on the screen of the LCD. By changing the display position of the fixation target on the screen of the LCD, the projected position of the fixation target on the fundus of the subject's eye E can be changed. The display position of the fixation target on the LCD can be designated by the user using the operation unit described below.

In some embodiments, the ophthalmic apparatus 1 includes an alignment system. In some embodiments, the alignment system includes an XY alignment system and a Z alignment system. The XY alignment system is used for position matching between the optical system of the apparatus and the subject's eye E in a direction intersecting the optical axis of the optical system of the apparatus (objective lens 46). The Z alignment system is used for position matching between the optical system of the apparatus and the subject's eye E in a direction of the optical axis of the ophthalmic apparatus 1 (objective lens 46).

For example, the XY alignment system projects a bright spot (bright spot in the infrared region or near-infrared region) onto subject's eye E. The data processor described below acquires an anterior segment image of the subject's eye E on which the bright spot is projected, and obtains the displacement between the bright spot image drawn on the acquired anterior segment image and an alignment reference position. The controller described below relatively moves the optical system of the apparatus and the subject's eye E in the direction intersecting the direction of the optical axis so as to cancel the obtained displacement, using the movement mechanism.

For example, the Z alignment system projects alignment light in infrared region or the near-infrared region from a position away from the optical axis of the optical system of the apparatus, and receives the alignment light reflected on the anterior segment of the subject's eye E. The data processor 200 specifies a distance to the subject's eye E with respect to the optical system of the apparatus, from the light receiving position of the alignment light that changes in accordance with the distance to the subject's eye E with respect to the optical system of the apparatus. The controller 100 relatively moves the optical system of the apparatus and the subject's eye E in the direction of the optical axis using the movement mechanism (movement mechanism 1D) so that the specified distance becomes a predetermined working distance.

In some embodiments, the function of the alignment system is realized by two or more anterior segment cameras arranged at positions away from the optical axis of the optical system of the apparatus. For example, as disclosed in Japanese Unexamined Patent Application Publication No. 2013-248376, the data processor described below analyzes the anterior segment images of subject's eye E substantially simultaneously acquired using the two or more anterior segment cameras, and specifies a three-dimensional position of the subject's eye E using known trigonometry. The controller described below controls the movement mechanism (movement mechanism 1D) to relatively move the optical system of the apparatus and the subject's eye E three-dimensionally so that the optical axis of the optical system of the apparatus substantially coincides with an axis of the subject's eye E and the distance of the optical system of the apparatus with respect to the subject's eye E is a predetermined working distance.

[Configuration of Control System]

Subsequently, a control system of the ophthalmic apparatus 1 will be described.

Figure 11:
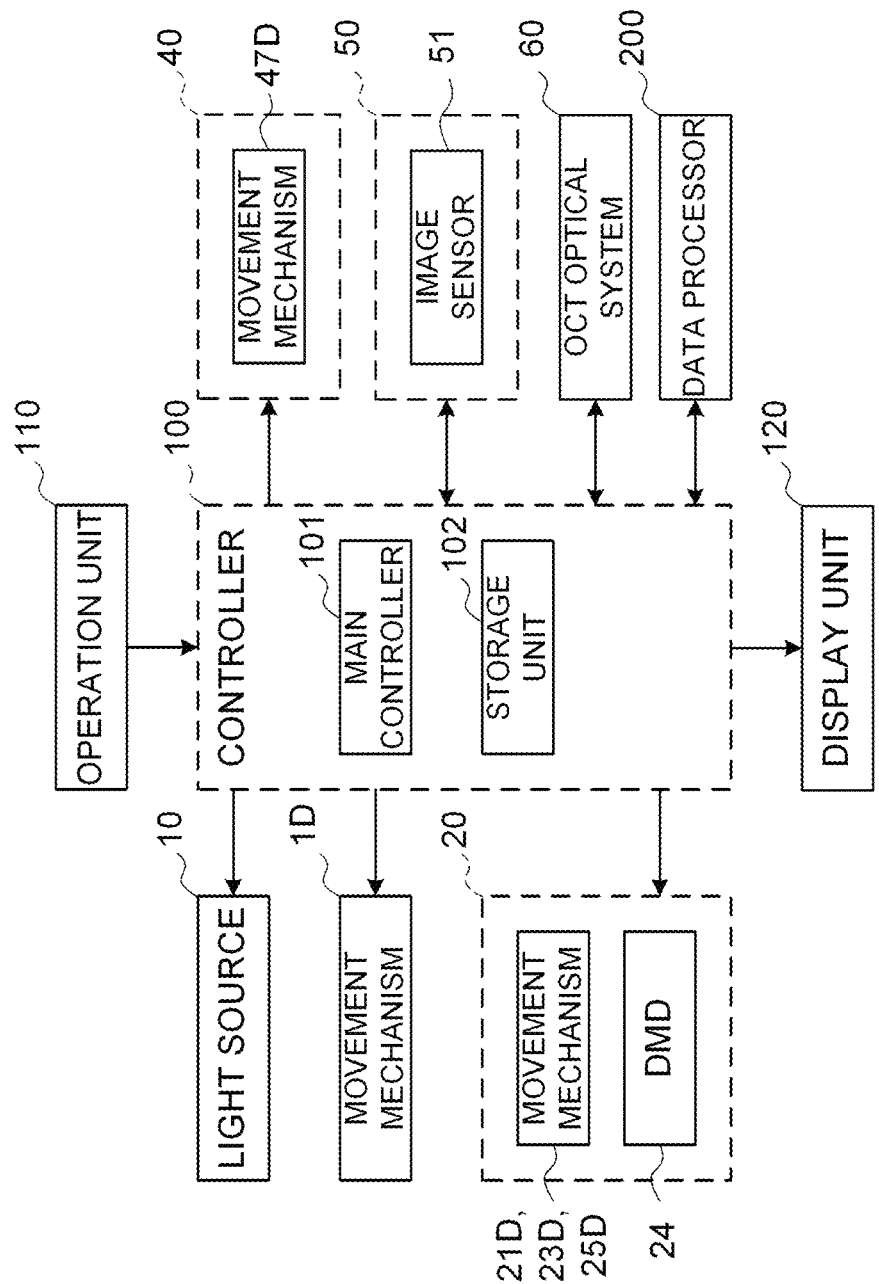
FIG. 11 is a diagram illustrating an example of the configuration of a control system of the ophthalmic apparatus according to the first embodiment.

FIG. 11 shows a block diagram of an example of the configuration of the control system of the ophthalmic apparatus 1 according to the first embodiment. In FIG. 11, parts similar to those in FIG. 1 are denoted by the same reference symbols, and description thereof is omitted as appropriate.

As shown in FIG. 11, the control system of the ophthalmic apparatus 1 is configured with a controller 100 as a center. It should be noted at least a part of the configuration of the control system may be included in the ophthalmic apparatus 1.

(Controller 100)

The controller 100 controls each part of the ophthalmic apparatus 1. The controller 100 includes a main controller 101 and a storage unit 102. The main controller 101 includes a processor and executes the control processing of each part of the ophthalmic apparatus 1 by executing processing according to the program(s) stored in the storage unit 102.

(Main Controller 101)

The main controller 101 performs control for the light source 10, movement mechanisms 1D, control for the illumination optical system 20, control for the imaging optical system 40, control for the imaging device 50, control for the OCT optical system 60, and control for the data processor 200.

Examples of the control for the light source 10 include switching the light source on and off (or switching the wavelength region of the light), and changing the light amount of the light or the light intensity of the light output from the light source.

The movement mechanism 1D relatively moves the subject's eye E and the optical system of the apparatus (the illumination optical system 20, the projection optical system 35, and the imaging optical system 40) included in the ophthalmic apparatus 1 using a known mechanism. The movement mechanism 1D three-dimensionally moves the relative position of the optical system of the apparatus to the subject's eye E, under the control from the main controller 101. Thereby, the relative position of the optical system of the apparatus to the subject's eye E is changed in at least one of the X, Y, and Z directions. The control for the movement mechanism 1D is performed in alignment and/or tracking. Here, tracking is to move the optical system of the apparatus according to the movement (eye movement, etc.) of the subject's eye E. To perform tracking, alignment and focusing are performed in advance, for example. The tracking is a function that maintains a suitable positional relationship, in which alignment and focusing have been adjusted, by moving the optical system of the apparatus in real time according to the position or the orientation of the subject's eye E based on the image obtained by imaging the subject's eye E. The image used for tracking may be a moving image or a plurality of still images in a time series acquired sequentially.

Example of the control for the illumination optical system 20 include a control for the movement mechanisms 21D, 23D, and 25D, and a control for the DMD 24.

The movement mechanism 21D moves the iris aperture 21 in the optical axis direction of the illumination optical system 20 (along the optical path of the illumination light). The main controller 101 can control the movement mechanism 21D in accordance with the state of the subject's eye E to arrange the iris aperture 21 at the position corresponding to the state of the subject's eye E. Examples of the state of the subject's eye E includes a shape of the fundus Ef, a dioptric power, and an axial length. The dioptric power can be obtained from a known eye refractive power measurement apparatus as disclosed in Japanese Unexamined Patent Application No. 61-293430 or Japanese Unexamined Patent Application Publication No. 2010-259495, for example. The axial length can be obtained from a known axial length measurement apparatus or a measurement value acquired by an optical coherence tomography.

The movement mechanism 23D moves relay lens 23 in the optical axis direction of the illumination optical system 20. The main controller 101 can control the movement mechanism 23D in accordance with the state of the subject's eye E to arrange the relay lens 23 at the position corresponding to the state of the subject's eye E.

The movement mechanism 25D moves the relay lens 25 in the optical axis direction of the illumination optical system 20. The main controller 101 can control the movement mechanism 25D in accordance with the state of the subject's eye E to arrange the relay lens 25 at the position corresponding to the state of the subject's eye E.

For example, the storage unit 102 stores first control information. In the first control information, the positions of the relay lens 25 on the optical axis of the illumination optical system 20 are associated with the dioptric powers in advance. The main controller 101 specifies the position of the relay lens 25 corresponding to the dioptric power by referring to the first control information, and controls the movement mechanism 25D so as to arrange the relay lens 25 at the specified position.

Here, as the relay lens 25 moves, the position of the iris aperture 21 shifts from the position substantially conjugate optically to the iris of the subject's eye E. In this case, as described above, the main controller 101 can control the movement mechanism 23D to arrange the position of the iris aperture 21 at a position substantially conjugate optically to the iris of the subject's eye E.

Examples of the control for the DMD 24 include a control for the length in the slit direction of the illumination light, a control for the slit width of the illumination light, a control for the position and the shape of the illumination region on the fundus Ef, and a control for the movement direction and the movement speed of the illumination region on the fundus Ef.

The control for the imaging optical system 40 includes a control for a movement mechanism 47D. The movement mechanism 47D moves the focusing lens 47 in the optical axis direction of the imaging optical system 40. The main controller 101 can control the movement mechanism 47D based on an analysis result of the image acquired using the image sensor 51. Further, the main controller 101 can control the movement mechanism 47D based on a content of operation of the user using an operation unit 110 described below.

Examples of the control for the imaging device 50 include a control for the image sensor 51 in synchronization with the irradiation timing of the illumination light on the fundus Ef using the DMD 24 (rolling shutter control). Examples of the control for the image sensor 51 include a control for the opening range on the light receiving surface corresponding to the illumination region of the illumination light on the fundus Ef, and a control for capturing the light receiving result obtained using the light receiving element in the opening range. Examples of the control for capturing the light receiving result include the reset control, the exposure control, the charge transfer control, and the output control. Further, time Tr required for the reset control, time (exposure time) Te required for the exposure control, time Tc required for the charge transfer control, and time Tout required for the output control, etc., can be changed.

Examples of the control for the OCT optical system 60 include a control for the OCT light source, a control for difference of the optical path length between the measurement light and the reference light, a control for focusing of the measurement light, a control for polarizing the measurement light or the reference light, and a control for detecting the interference light.

Example of the control for the data processor 200 include various kinds of image processing and various kinds of analysis processing on the light receiving results acquired from the image sensor 51. Examples of the image processing include noise removal processing on the light receiving results, brightness correction processing for easily identifying a predetermined site depicted in the light receiving image based on the light receiving results, and forming processing of the OCT image (two-dimensional image, three-dimensional image, OCT angiogram) based on the detection result of the interference light). Examples of the analysis processing include a specifying processing of the site of interest, a specifying processing of the content of tracking control, and a specifying processing of the in-focus state.

The data processor 200 can form the light receiving image corresponding to the arbitrary opening range based on the light receiving result(s) read out from the image sensor 51 using the rolling shutter method, under the control from the main controller 101 (controller 100). The data processor 200 can sequentially form light receiving light images corresponding to the opening ranges and can form an image of the subject's eye E from a plurality of formed light receiving images.

The data processor 200 can perform the processing of specifying the site of interest on the fundus Ef for tracking control. For example, the data processor 200 specifies an image region corresponding to a site of interest on the fundus Ef based on pixel values of the image of the fundus Ef. In some embodiments, the image region corresponding to the site of interest in the image of the fundus Ef acquired in the fundus imaging mode is specified, and the image region corresponding to the site of interest within the imaging region in the tracking mode is specified based on the positional relationship between the imaging region in the fundus imaging mode and the imaging region in the tracking mode.

In some embodiments, the data processor 200 specifies a displacement of the position of the site of interest in the image of the fundus Ef acquired in the tracking mode with reference to the position of the site of interest (imaging region) depicted in the reference image, and specifies the content of the tracking control based on the specified displacement. Examples of the reference image include a predetermined image and an image of the fundus Ef acquired one or more frames before the frame to be analyzed in the tracking mode. The main controller 101 can control the movement mechanism 1D based on the specified content of the tracking control to perform tracking control.

In some embodiments, the data processor 200 specifies the displacement of the position of the site of interest in the image of the fundus Ef obtained in the tracking mode with respect to a predetermined reference position, and specifies the content of the tracking control based on the specified displacement. Examples of the reference position include a position corresponding to the optical axis of the imaging optical system 40 (illumination optical system 20), and a predetermined position (center position, etc.) in the image of the fundus Ef.

The data processor 200 includes a processor, and realizes the above functions by performing processing corresponding to the program(s) stored in the storage unit or the like.
(Storage Unit 102)

The storage unit 102 stores various computer programs and data. The computer programs include an arithmetic program and a control program for controlling the ophthalmic apparatus 1.
(Operation Unit 110)

The operation unit 110 includes an operation device or an input device. The operation unit 110 includes buttons and switches (e.g., operation handle, operation knob, etc.) and operation devices (e.g., mouse, keyboard, etc.) provided in the ophthalmic apparatus 1. In addition, the operation unit 110 may include any operation device or any input device, such as a trackball, a control panel, a switch, a button, a dial, etc.

(Display Unit 120)

The display unit 120 displays the image of the subject's eye E generated by data processor 200. The display unit 120 is configured to include a display device such as a flat panel display such as an LCD (Liquid Crystal Display). In addition, the display unit 120 may include various types of display devices such as a touch panel and the like provided in the housing of the ophthalmic apparatus 1.

It should be noted that the operation unit 110 and the display unit 120 do not need to be configured to be separate devices. For example, a device like a touch panel, which has a display function integrated with an operation function, can be used. In this case, the operation unit 110 includes the touch panel and a computer program. The content for the operation unit 110 is fed to the controller 100 as electrical signals. Moreover, operations and inputs of information may be performed using a graphical user interface (GUI) displayed on the display unit 120 and the operation unit 110. In some embodiments, the functions of the display unit 120 and the operation unit 110 are realized a touch screen.

The DMD 24 is an example of the "light modulator" according to the embodiments. The data processor 200 is an example of the "image forming unit" according to the embodiments. The movement mechanism 1D is an example of the "first movement mechanism" according to the embodiments. The movement mechanism 25D is an example of the "second movement mechanism" according to the embodiments. The movement mechanism 21D or the movement mechanism 23D is an example of the "third movement mechanism" according to the embodiments.

[Operation]

Next, the operation of the ophthalmic apparatus 1 will be described. Hereinafter, an example of the operation in a case where the tracking control is performed using the image of the fundus Ef acquired in the tracking mode and the wide-angle image of the fundus Ef is acquired in the fundus imaging mode during tracking control will be described.

Figure 13A:
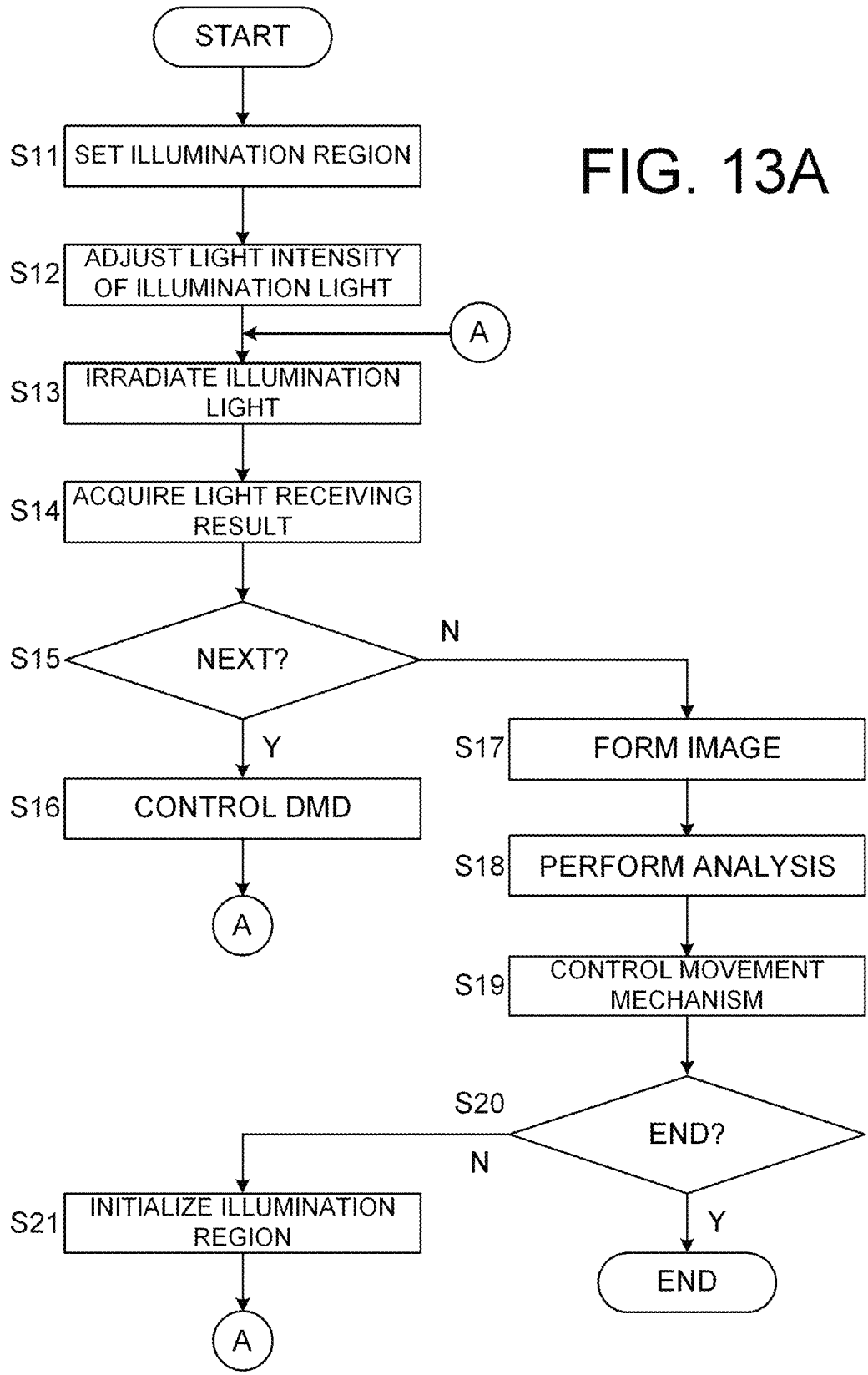
FIG. 13A is a flow illustrating an example of the operation of the ophthalmic apparatus according to the first embodiment.
Figure 13B:
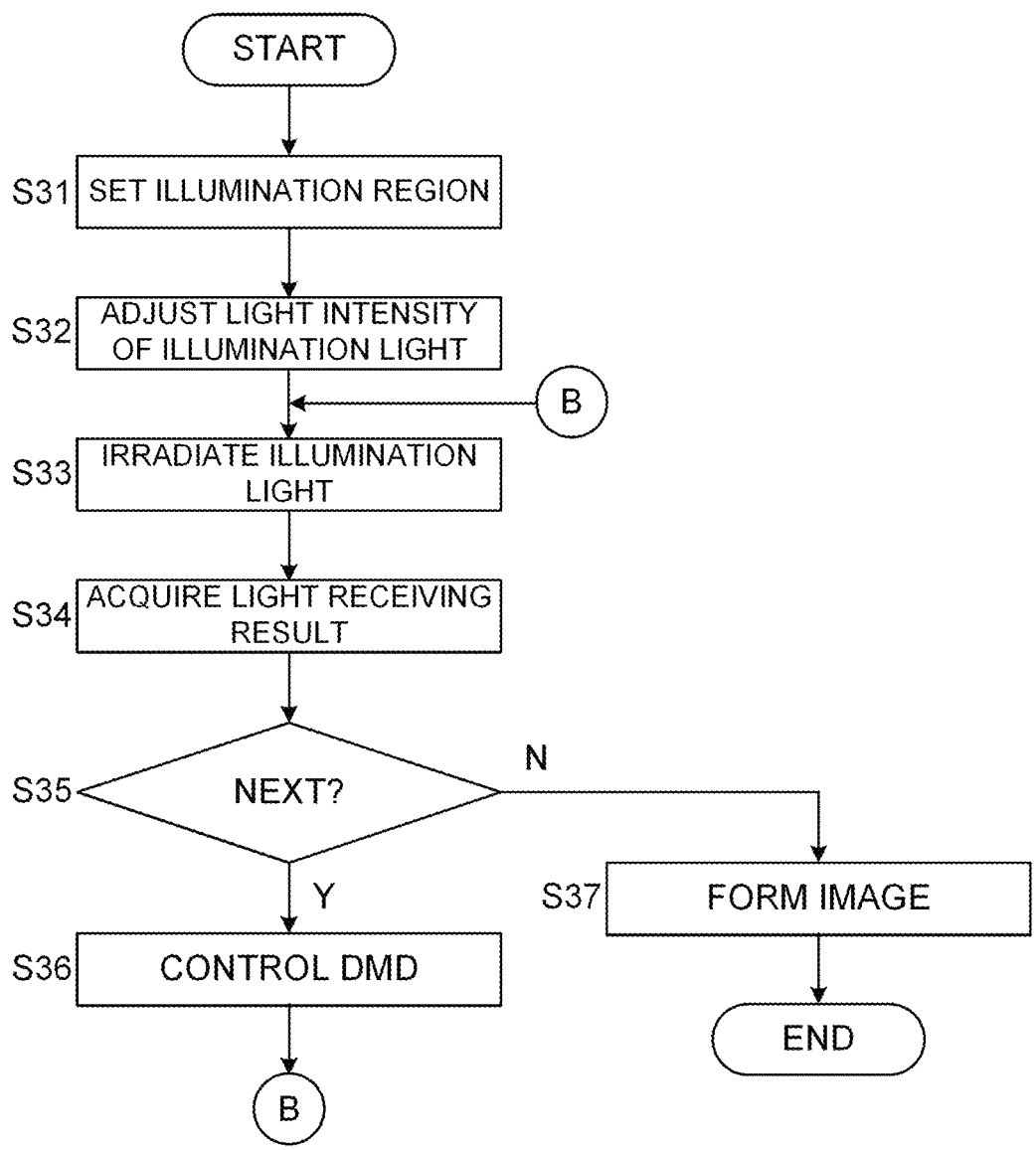
FIG. 13B is a flow illustrating an example of the operation of the ophthalmic apparatus according to the first embodiment.

FIG. 12, FIG. 13A, and FIG. 13B show flowcharts of examples of the operation of the ophthalmic apparatus 1 according to the embodiments. FIG. 12 represents a flowchart of an example of the operation when the fundus imaging is performed by switching the imaging mode. FIG. 13A shows a flowchart of an example of the operation of step S4 in FIG. 12. FIG. 13B shows a flowchart of an example of the operation of step S6 in FIG. 12. The storage unit 102 stores computer programs for realizing the processing shown in FIG. 12, FIG. 13A, and FIG. 13B. The main controller 101 operates according to the computer programs, and thereby the main controller 101 performs the processing shown in FIG. 12, FIG. 13A, and FIG. 13B.

Here, it is assumed that the alignment of the optical system of the apparatus with respect the subject's eye E using the alignment system (not shown) is completed, and that the fixation target is projected onto the fundus of the subject's eye E to guide the subject's eye E to a desired fixation position using the fixation projection system (not shown).

(S1: Acquire Dioptric Power)

First, the main controller 101 acquires the dioptric power of the subject's eye E from an external ophthalmic measurement apparatus or an electronic medical record.

(S2: Move Lens)

Next, the main controller 101 controls the movement mechanism 25D in accordance with the dioptric power of the subject's eye E acquired in step S1 to change the position of the relay lens 25 on the optical axis of the illumination optical system 20. Thereby, the DMD 24 is placed at a position substantially conjugate optically to the fundus Ef.

Specifically, the main controller 101 specifies the position of the relay lens 25 corresponding to the dioptric power by referring to the first control information stored in the storage unit 102, and controls the movement mechanism 25D so as to arrange the relay lens 25 at the specified position. In some embodiments, the main controller 101 further controls the movement mechanism 23D to cancel the shift of the position substantially conjugate optically to the iris caused by the movement of the relay lens 25.

(S3: Tracking Mode?)

Subsequently, the main controller 101 determines whether or not to the imaging mode is set to the tracking mode. For example, the main controller 101 determines whether or not the imaging mode is set to the tracking mode based on the content of the operation by the user using the operation unit 110.

When it is determined that the imaging mode is set to the tracking mode (S3: Y), the operation of the ophthalmic apparatus 1 proceeds to step S4. When it is determined that the imaging mode is set to the fundus imaging mode (S3: N), the operation of the ophthalmic apparatus 1 proceeds to step S7.

(S4: Start Tracking Control)

In step S3, when it is determined that the imaging mode is set to the tracking mode (S3: Y), the main controller 101 start the tracking control. The details of step S4 will be described below.

(S5: Perform OCT Measurement)

Subsequently, the main controller 101 controls the OCT optical system 60 to perform OCT measurement. That is, the OCT measurement is performed during the tracking control that has been started in step S4. In the OCT measurement, detecting the interference light, forming the OCT image or the OCT angiogram based on the detection result of the interference light, etc. are performed.

In step S5, the measurement using the measurement optical system provided in the ophthalmic apparatus can be performed during the tracking control that has been performed in step S4. For example, it should be noted that when the measurement optical system provided in the ophthalmic apparatus has a function such as a refractive power measurement function, the refractive power measurement, etc. is performed during the tracking control that has been started in step S4.

(S6: Set to Fundus Imaging Mode)

In step S3, when it is determined that the imaging mode is not set to the tracking mode (S3: N), the main controller 101 perform the fundus imaging. The details of step S6 will be described below.

The processing in step S5 or in step S6 is terminated, the operation of the ophthalmic apparatus 1 is terminated (END).

Step S4 in FIG. 12 is performed according to the flow shown in FIG. 13A.

(S11: Set Illumination Region)

When the imaging mode is set to the tracking mode in step S3 in FIG. 12, the main controller 101 controls the DMD 24 to set the illumination region with the size for the tracking mode to the fundus Ef (illumination region control step, first illumination region control step).

(S12: Adjust Light Intensity of Illumination Light)

Subsequently, the main controller 101 controls at least one of the light source 10 and the variable neutral density filter 11 to adjust the light intensity of the illumination light generated by the illumination optical system 20 (light intensity control step, first light intensity control step). The main controller 101 changes the light intensity of the illumination light so that the irradiance on the anterior segment of the subject's eye remains constant.

(S13: Irradiate Illumination Light)

Next, in order to start fundus imaging in the tracking mode, the main controller 101 controls the light source 10 and the DMD 24 to irradiate the slit-shaped illumination light onto the illumination region set in step S11.

(S14: Acquire Light Receiving Result)

The main controller 101 acquires the light receiving results of the pixels in the opening range on the light receiving surface of the image sensor 51 corresponding to the illumination region of the illumination light irradiated onto the fundus Ef in step S13 (image sensor control step), as described above.

(S15: Next?)

The main controller 101 determines whether or not an illumination region (illuminated position) should be irradiated with the illumination light next. The main controller 101 can determine whether or not the illumination region should be irradiated with the illumination light next, by determining whether or not the illumination region of the illumination light that is moved sequentially has covered a predetermined imaging region of the fundus Ef.

When it is determined that the illumination region should be irradiated with the illumination light next (S15: Y), the operation of the ophthalmic apparatus 1 proceeds to step S16. When it is determined that the illumination region should not be irradiated with the illumination light next (S15: N), the operation of the ophthalmic apparatus 1 proceeds to step S17.

(S16: Control DMD)

In step S15, when it is determined that the illumination region should be irradiated with the illumination light next (S15: Y), the main controller 101 controls the DMD 24 to set the illumination region at the position to be irradiated next. And then, the operation of the ophthalmic apparatus 1 proceeds to step S13.

(S17: Form Image)

In step S15, when it is determined that the illumination region should not be irradiated with the illumination light next (S15: N), the main controller 101 controls the data processor 200 to form the image of the subject's eye E (first image forming step).

The data processor 200 forms the image of the subject's eye E from the light receiving results obtained repeatedly while changing the illumination region of the illumination light so as to cover the imaging region on the fundus Ef in step S13 and in step S14.

(S18: Perform Analysis)

Subsequently the main controller 101 controls the data processor 2001 to analyze the image formed in step S17 to specify the content of the tracking control.

The data processor 200 specifies the image region corresponding to the optic disc on the fundus Ef based on pixel values of the image of the fundus Ef formed in step S17, for example. After that, the data processor 200 specifies the displacement of the position of the image region specified in the current frame with reference to the position of the image region corresponding to the optic disc in the image of the fundus Ef acquired before the current frame, and specifies the content of the tracking control based on the specified displacement. Examples of the content of the tracking control include the shift amount and shift direction of the relative position of the optical system of the apparatus to the subject's eye E.

(S19: Control Movement Mechanism)

Next, the main controller 101 controls the movement mechanism 1D based on the content of the tracking control specified in step S18 to change the relative position of the optical system of the apparatus to the subject's eye E (tracking control step).

(S20: ENDY?)

Subsequently, the main controller 101 determines whether or not the tracking control should be ended. For example, the main controller 101 determines whether or not the tracking control should be ended based on the instruction from the user using the operation unit 110. For example, the main controller 101 determines whether or not the tracking control should be ended by determining whether or not the fundus imaging in step S8 has been terminated.

When it is determined that the tracking control should be ended (S20: Y), the ophthalmic apparatus 1 terminates the tracking control (END). When it is determined that the tracking control should not be ended (S20: N), the operation of the ophthalmic apparatus 1 proceeds to step S21.

(S21: Initialize Illumination Region)

In step S20, when it is determined that the tracking control should not be ended (S20: N), the main controller 101 initializes the illumination region in order to set the illumination region with the size for the tracking mode for the fundus Ef again. The operation of the ophthalmic apparatus 1 proceeds to step S13.

Step S6 in FIG. 12 is performed according to the flow shown in FIG. 13B.

(S31: Set Illumination Region)

When the imaging mode is set to the fundus imaging mode in step S5 in FIG. 12, the main controller 101 controls the DMD 24 to set the illumination region with the size for the fundus imaging mode to the fundus Ef (illumination region control step, second illumination region control step).

(S32: Adjust Light Intensity of Illumination Light)

Subsequently, the main controller 101 controls at least one of the light source 10 and the variable neutral density filter 11 to adjust the light intensity of the illumination light generated by the illumination optical system 20 (light intensity control step, second light intensity control step). The main controller 101 changes the light intensity of the illumination light so that the irradiance on the anterior segment of the subject's eye remains constant.

(S33: Irradiate Illumination Light)

Next, in order to start fundus imaging in the fundus imaging mode, the main controller 101 controls the light source 10 and the DMD 24 to irradiate the slit-shaped illumination light onto the illumination region set in step S31.

(S34: Acquire Light Receiving Result)

The main controller 101 acquires the light receiving results of the pixels in the opening range on the light receiving surface of the image sensor 51 corresponding to the illumination region of the illumination light irradiated onto the fundus Ef in step S33 (image sensor control step), as described above.

(S35: Next?)

The main controller 101 determines whether or not an illumination region (irradiated position) should be irradiated with the illumination light next. The main controller 101 can determine whether or not the illumination region should be irradiated with the illumination light next, by determining whether or not the illumination region of the illumination light that is moved sequentially has covered a predetermined imaging region of the fundus Ef.

When it is determined that the illumination region should be irradiated with the illumination light next (S35: Y), the operation of the ophthalmic apparatus 1 proceeds to step S36. When it is determined that the illumination region should not be irradiated with the illumination light next (S35: N), the operation of the ophthalmic apparatus 1 proceeds to step S37.

(S36: Control DMD)

In step S35, when it is determined that the illumination region should be irradiated with the illumination light next (S35: Y), the main controller 101 controls the DMD 24 to set the illumination region at the position to be irradiated next. And then, the operation of the ophthalmic apparatus 1 proceeds to step S33.

(S37: Form Image)

In step S35, when it is determined that the illumination region should not be irradiated with the illumination light next (S35: N), the main controller 101 controls the data processor 200 to form the image of the subject's eye E (second image forming step).

The data processor 200 forms the image of the subject's eye E from the light receiving results obtained repeatedly while changing the illumination region of the illumination light so as to cover the imaging region on the fundus Ef in step S33 and in step S34.

This terminates the processing of step S6 in FIG. 2 (END).

As described above, when the imaging mode is set to the tracking mode (first imaging mode), the main controller 101 controls the data processor 200 to form the image for tracking (first image) based on the light receiving results obtained by illuminating the predetermined illumination region (first illumination region) corresponding to the tracking mode with the illumination light. The main controller 101 controls the movement mechanism JD based on the formed image to perform tracking control. In contrast, when the imaging mode is set to the fundus imaging mode (second imaging mode), the main controller 101 controls the data processor 200 to form the image of the fundus Ef (second image) based on the light receiving results obtained by illumination the illumination region (second illumination region) that corresponds to the fundus imaging mode and is wider than the above illumination region.

According to the first embodiment, the ophthalmic apparatus capable of imaging the site of interest at high speed with a simple configuration can be provided. In particular, the illumination light is generated so that the light intensity increases when the size of the imaging region is reduced. Thereby, the light intensity of the returning light from the site of interest cab be increased, and the SNR of the light receiving results of the returning light can be improved and the image quality of the image formed based on the light receiving results of the returning light can be enhanced. As a result, the site of interest can be observed in detail and the images necessary for highly accurate tracking can be acquired.

Second Embodiment

The configuration of the ophthalmic apparatus according to the embodiments is not limited to the configuration shown in FIG. 1. The ophthalmic apparatus according to a second embodiment has a simpler configuration and has the same effect as the ophthalmic apparatus 1 according to the first embodiment. In the following, the ophthalmic apparatus according to the second embodiment will be described focusing on differences from the ophthalmic apparatus 1 according to the first embodiment.

Figure 14:
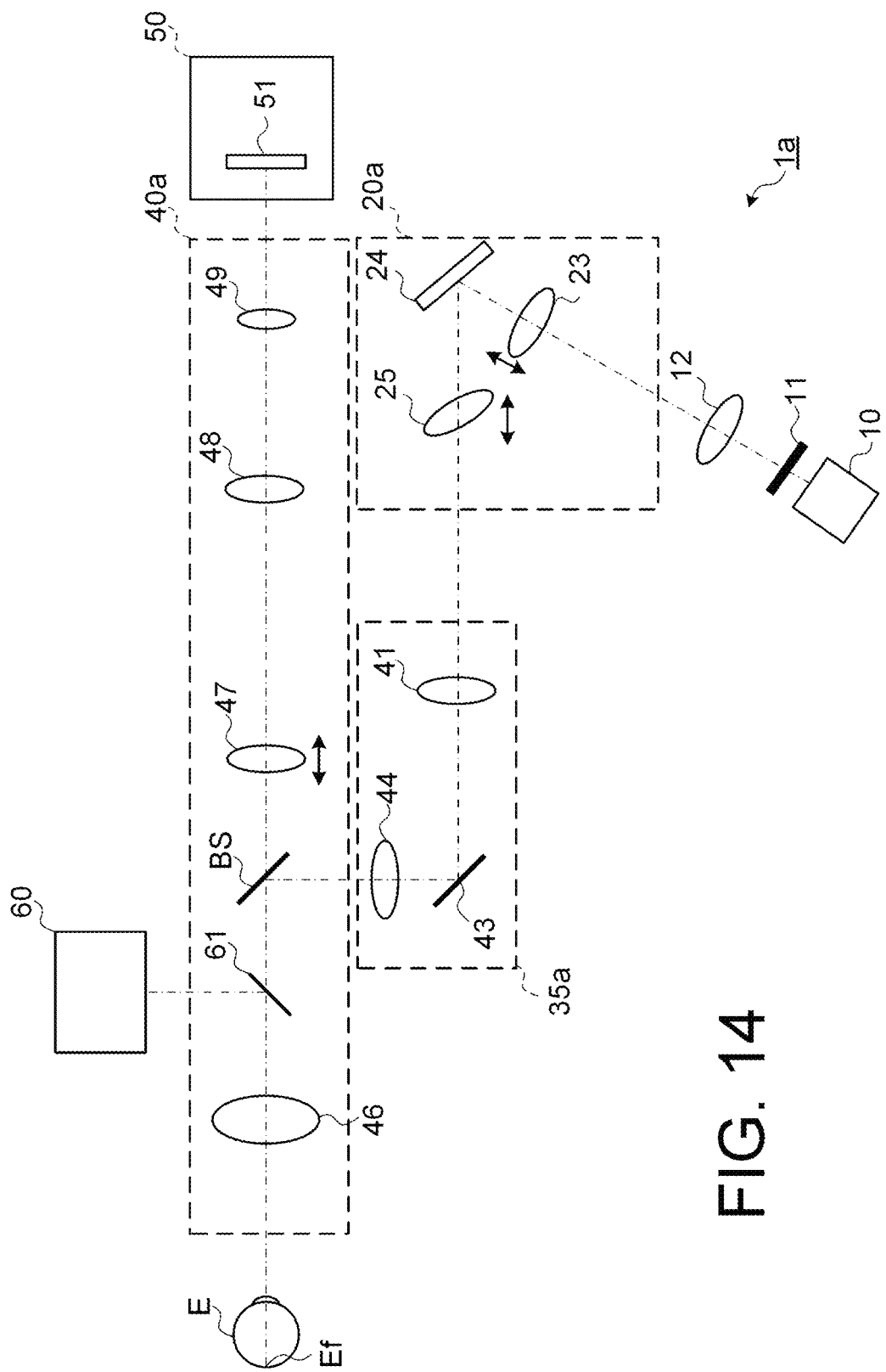
FIG. 14 is a schematic diagram illustrating an example of a configuration of an optical system of the ophthalmic apparatus according to a second embodiment.

FIG. 14 illustrates an example of a configuration of an optical system of the ophthalmic apparatus according to the second embodiment. In FIG. 14, parts similar to those in FIG. 1 are denoted by the same reference symbols, and description thereof is omitted as appropriate.

The configuration of the ophthalmic apparatus 1a according to the second embodiment differs from that of the ophthalmic apparatus 1 according to the first embodiment mainly in that an illumination optical system 20a is provided instead of the illumination optical system 20, that a projection optical system 35a is provided instead of the projection optical system 35, and that an imaging optical system 40a is provided instead of the imaging optical system 40.

The configuration of the illumination optical system 20a differs from that of the illumination optical system 20 in that the iris aperture 21 is removed. The configuration of the projection optical system 35a differs from that of the projection optical system 35 in that the black point plate 42 is removed. The configuration of the imaging optical system 40a differs from the configuration of the imaging optical system 40 in that a beam splitter BS is provided instead of the perforated mirror 45.

The beam splitter BS reflects the illumination light from the projection optical system 35a to guide to the objective lens 46, and transmits through the returning light of the illumination light transmitted through the objective lens 46 toward the focusing lens 47.

The operation of the ophthalmic apparatus 1 according to the second embodiment is similar to the operation of the ophthalmic apparatus 1 according to the first embodiment. Thus, the detailed description of the operation will be omitted.

The beam splitter BS is an example of the "optical path coupling member" according to the embodiments.

As described above, according to the second embodiment, the same effect as the first embodiment can be obtained with a simpler configuration compared to the first embodiment.

Third Embodiment

In the above embodiments, a case where the slit-shaped illumination is generated using the light modulator such as the DMD 24. However, the configuration of the ophthalmic apparatus according to the embodiments is not limited to this. The ophthalmic apparatus according to a third embodiment generates the slit-shaped illumination light using a slit with an aperture formed, and moves the illumination region of the illumination light so as to cover the imaging region on the fundus Ef by deflecting the slit-shaped illumination light using an optical scanner. In the following, the ophthalmic apparatus according to the third embodiment will be described focusing on differences from the ophthalmic apparatus 1 according to the first embodiment.

Figure 15:
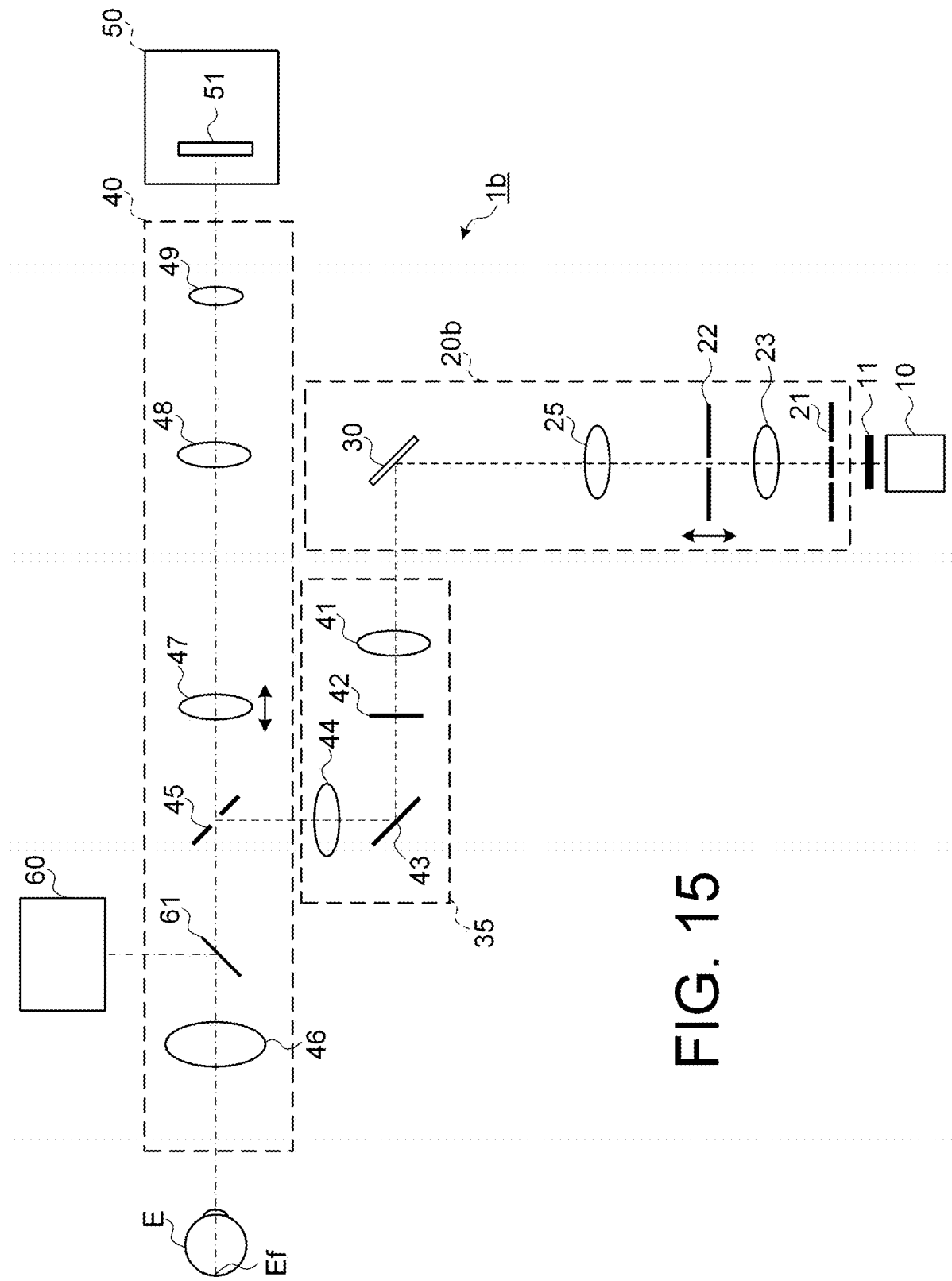
FIG. 15 is a schematic diagram illustrating an example of a configuration of an optical system of the ophthalmic apparatus according to a third embodiment.

FIG. 15 illustrates an example of a configuration of an optical system of the ophthalmic apparatus according to the third embodiment. In FIG. 15, parts similar to those in FIG. 1 are denoted by the same reference symbols, and description thereof is omitted as appropriate. It should be noted that in FIG. 15, the condenser lens 12 in FIG. 1 is assumed to be included in the light source 10.

The configuration of the ophthalmic apparatus 1b according to the third embodiment differs from that of the ophthalmic apparatus 1 according to the first embodiment in that an illumination optical system 20b is provided instead of the illumination optical system 20.

The illumination optical system 20b includes the iris aperture 21, a slit 22, the relay lenses 23 and 25, and an optical scanner 30. The slit 22 is arranged between the iris aperture 21 and the optical scanner 30. The relay lens 23 is arranged between the iris aperture 21 and the slit 22. The relay lens 25 is arranged between the optical scanner 30 and the slit 22.

(Slit 22)

The slit 22 (specifically, aperture(s) described below) can be arranged at a position substantially conjugate optically to the fundus Ef of the subject's eye E. For example, in the slit 22, the aperture is formed in a direction corresponding to a line direction (row direction) that is read out from the image sensor 51 using the rolling shutter method. The aperture formed in the slit 22 defines an illumination pattern of the illumination light on the fundus Ef of the subject's eye E.

The slit 22 can be moved in the optical axis direction of the illumination optical system 20b using a movement mechanism (movement mechanism 22D described below). The movement mechanism moves the slit 22 in the optical axis direction, under the control from the controller 100b described below. For example, the controller 100b controls the movement mechanism in accordance with the state of the subject's eye E. This allows to move the position of the slit 22 in accordance with the state of the subject's eye E (specifically, the dioptric power or the shape of the fundus Ef).

The slit 22 is configured so that the shape (size) of the aperture can be changed in accordance with the imaging mode.

Figure 16:
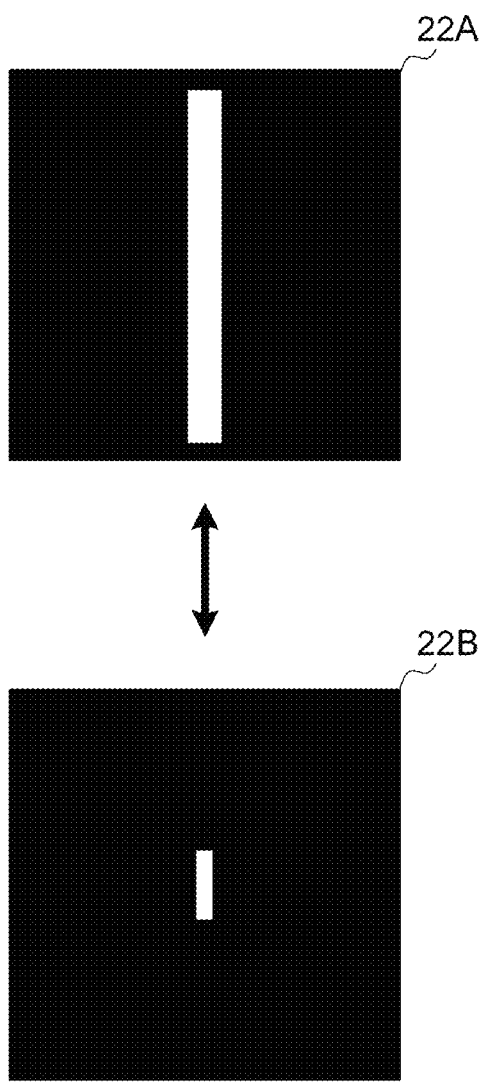
FIG. 16 is an explanatory diagram of an example of the configuration of the optical system of the ophthalmic apparatus according to the third embodiment.

FIG. 16 illustrates a diagram explaining an example of the configuration of the slit 22 according to the third embodiment.

When the imaging mode is designated to the tracking mode, the slit 22 is changed to the slit-shaped aperture for irradiating the illumination light onto the illumination region for the tracking mode (slit 22B in FIG. 16). Further, when the imaging mode is designated to the fundus imaging mode, the slit 22 is changed to the slit-shaped aperture for irradiating the illumination light onto the illumination region for the fundus imaging mode (slit 22A in FIG. 16). In other words, the size of the slit-shaped aperture in the tracking mode is smaller than the size of the slit-shaped aperture in the fundus imaging mode.

For example, the slit 22 includes two or more slits with different shapes of apertures, and selectively arranged the two or more slits in the optical path of light from the light source 10 in accordance with the imaging mode. For example, the slit 22 includes a liquid crystal shutter, and forms an aperture having the shape corresponding to the imaging mode.

In some embodiments, the length in the slit direction of the aperture in the tracking mode is shorter than the length in the slit direction of the aperture in the fundus imaging mode. In some embodiments, the slit width of the aperture in the tracking mode is narrower than the slit width of the aperture in the fundus imaging mode. In some embodiments, the length in the slit direction of the aperture in the tracking mode is shorter than the length in the slit direction of the aperture in the fundus imaging mode, and the slit width of the aperture in the tracking mode is narrower than the slit width of the aperture in the fundus imaging mode. In some embodiments, the length in the slit direction is the same in the fundus imaging mode and the tracking mode, and the slit width of the aperture in the tracking mode is narrower than the slit width of the aperture in the fundus imaging mode. In some embodiments, the slit width is the same in the fundus imaging mode and the tracking mode, and the length in the slit direction of the aperture in the tracking mode is shorter than the length in the slit direction of the aperture in the fundus imaging mode.

In some embodiments, the slit 22 is configured so that at least one of the position of the aperture and the shape of the aperture can be changed in accordance with the state of the subject's eye E without being moved in the optical axis direction. The function of the slit 22 with this configuration is, for example, realized by a liquid crystal shutter.

The light from the light source 10 that has passed through the aperture formed in the iris aperture 21 is output as the slit-shaped illumination by passing through the aperture formed in the slit 22. The slit-shaped illumination light is transmitted through the relay lens 23, and is guided to the optical scanner 30.

(Optical Scanner 30)

The optical scanner 30 is placed at a position substantially conjugate optically to the iris of the subject's eye E. The optical scanner 30 deflects the slit-shaped illumination light transmitted through the relay lens 23 (slit-shaped light passing through the aperture(s) formed in the slit 22). Specifically, the optical scanner 30 deflects the slit-shaped illumination light for sequentially illuminating a predetermined illumination region on the fundus Ef to guide the illumination light to the projection optical system 35, while changing the deflection angle within a predetermined deflection angle range with the iris or the vicinity of the iris of the subject's eye E as a scan center position. The optical scanner 30 can deflect the illuminating light one-dimensionally or two-dimensionally.

In case that the optical scanner 30 deflects the illumination light one-dimensionally, the optical scanner 30 includes a galvano scanner that deflects the illuminating light within a predetermined deflection angle range with reference to a predetermined deflection direction. In case that the optical scanner 30 deflects the illumination light two-dimensionally, the optical scanner 30 includes a first galvano scanner and a second galvano scanner. The first galvano scanner deflects the illumination light so as to move the illumination region of the illumination light in a horizontal direction orthogonal to the optical axis of the illumination optical system 20. The second galvano scanner deflects the illumination light deflected by the first galvano scanner so as to move the illumination region of the illumination light in a vertical direction orthogonal to the optical axis of the illumination optical system 20. Examples of scan mode for moving the illumination region of the illumination light using the optical scanner 30 include a horizontal scan, a vertical scan, a cross scan, a radial scan, a circle scan, a concentric scan, and a helical (spiral) scan.

Figure 17:
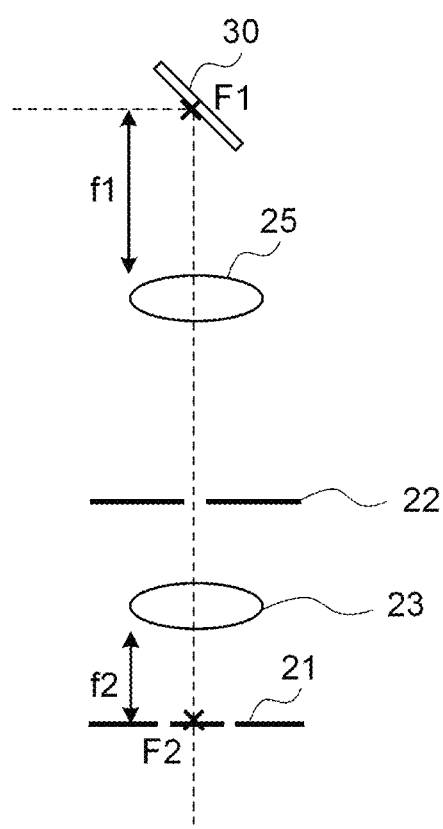
FIG. 17 is an explanatory diagram of an example of the configuration of the optical system of the ophthalmic apparatus according to the third embodiment.

FIG. 17 illustrates an example of the configuration of the illumination optical system 20b according to the third embodiment. In FIG. 17, components similar to those in FIG. 5 are given the same reference numerals. The description of such components is basically omitted.

A back focal position F1 of the relay lens 25 is arranged at a position substantially conjugate optically to the iris of the subject's eye E.

That is, the optical scanner 30, which is arranged at a position substantially conjugate optically to the iris of the subject's eye E as described above, is arranged at the back focal position F1 of the relay lens 25 or the vicinity of the back focal position F1. Therefore, even when the slit 22 is moved in the optical axis direction in accordance with the dioptric power of the subject's eye E, the size of the slit image (image formed by the light passing through the aperture formed in the slit 22) projected onto the fundus Ef does not change. This means that the projection magnification of the slit image onto the fundus Ef does not change even when the slit 22 moves in the optical axis direction.

According to the third embodiment, by arranging the optical scanner 30 at the back focal position F1 of the relay lens 25 (or the vicinity of the back focal position F1), the Badal optical system is configured with the relay lens 25, the relay lenses 41 and 42, and the objective lens 46.

This allows to keep the projected angle of view (projection magnification) of the slit image with reference to the visual axis of the subject's eye E (longitudinal and shorter directions of the slit 22) constant, regardless the dioptric power of the subject's eye E. As a result, the size of the slit image does not change regardless of the dioptric power of the subject's eye E. This allows to keep the deflection operation speed of the optical scanner 30 constant, and to simplify the control of the optical scanner 30.

In addition, since the projected angle of view (projection magnification) of the slit image with reference to the visual axis of the subject's eye E is constant regardless of the dioptric power of the subject's eye E, the illumination intensity of the slit image at the fundus Ef can be kept constant regardless of the dioptric power of the subject's eye E.

Further, in case of acquiring images at a predetermined imaging angle of view in the ophthalmic apparatus, since the projection magnification is constant as described above, this eliminates the need for a margin of the length in the longitudinal length of the slit 22 provided to acquire a slit image of a predetermined size.

Further, the iris aperture 21 is arranged at a front focal position F2 of the relay lens 23 or the vicinity of the front focal position F2.

That is, the back focal position F1 of the relay lens 25 is the position substantially conjugate optically to the iris of the subject's eye E, and the iris aperture 21 is arranged at the front focal position F2 of the relay lens 23. Therefore, the projection magnification from the iris aperture 21 to the optical scanner 30 (arranged at the back focal position F1) is determined by a focal distance f1 of the relay lens 25 and a focal distance 2 of the relay lens 23. In this case, the projection magnification is (f1/f2).

The ophthalmic apparatus according to the embodiments is required to form images of the iris aperture 21 with a predetermined size on the iris of the subject's eye E. When the projection magnification from the iris of the subject's eye E to the optical scanner 30 via the objective lens 46 is a known projection magnification, an image of the iris aperture 21 of a predetermined size should be projected on the optical scanner 30. In this case, the projection magnification from the iris aperture 21 to the optical scanner 30 is determined by the focal distance f1 of the relay lens 25 and the focal distance f2 of the relay lens 23. Therefore, by changing at least one of the focal distances f1 and f2, the image of the iris aperture 21 can be easily formed on the iris of the subject's eye E with a predetermined size. In some embodiments, while the focal distance f1 remains fixed, the focal distance 12 is changed alone.

In addition, for imaging the fundus Ef, it is desirable to use a light source that emits a high-intensity light. However, light sources available for general use (light sources that are mass-produced) are limited in the size of the emitting surface (luminous area, output luminous flux cross section size). Thereby, the image of the iris aperture 21 should be projected onto the optical scanner 30 with a projection magnification corresponding to the size of the emitting surface of the light source.

According to the present embodiment, by changing at least one of the focal distances f1 and f2, the projecting magnification from the iris aperture 21 to the optical scanner 30 can be changed. Thereby, the image of the iris aperture 21 with any size can be projected onto the optical scanner 30 with the desired size. This allows to project the image of the iris aperture 21 with a desired size onto the optical scanner 30 by simply changing at least one of the focal distances fil and f2 even when the size of the emitting surface of the light source is different and to improve the degree of freedom in designing optical systems. In particular, this allows to fix the movement amount of the slit 22 in response to changes in the dioptric power of the subject's eye E (sensitivity of the movement of the slit 22 in response to changes in the dioptric power) by fixing the focal distance f1 and changing the focal distance f2 alone, and to further improve the degree of freedom in designing optical systems.

According to the third embodiment, the effective diameter of one or more lenses constituting the relay lens 25 can be reduced.

The reason for this is that the slit 22, which is arranged at a position substantially conjugate optically to the fundus Ef of the subject's eye E, is arranged between the optical scanner 30 and the iris aperture 21. The slit 22 can be moved in the optical axis direction in accordance with the dioptric power of the subject's eye E. Here, the projection magnification from the iris aperture 21 to the optical scanner 30 is determined by the first distance, which is a distance between the optical scanner 30 and the relay lens 25, and the second distance, which is a distance between the iris aperture 21 and the relay lens 25. Thereby, when the first distance is shortened, the second distance should also be shortened. However, since it is necessary to maintain the conjugate relationship with the iris and the conjugate relationship with the fundus Ef while securing the space for movement of the slit 22 in the optical axis direction, the first distance becomes longer and the effective diameter of the relay lens 25 becomes larger. According to the present embodiment, by providing the relay lens 23, the projection magnification can be adjusted using the relay lens 23 even if the first distance is shortened. This allows to shorten the first distance while maintaining the conjugate relationship with the iris and the conjugate relationship with the fundus Ef and securing the space for movement of the slit 22 in the optical axis direction, and to reduce the effective diameter of the one or more lenses constituting the relay lens 25.

Further, since the effective diameter of the one or more lenses constituting the relay lens 25 can be reduced, the length of the optical system from the optical scanner 30 to the light source 10 can be reduced.

The slit-shaped illumination light generated as described above is deflected by the optical scanner 30, and is guided to the projection optical system 35. In the projection optical system 35, the illumination light deflected by the optical scanner 30 is transmitted through the relay lens 41, passes through the black point plate 42, is reflected by the reflective mirror 43 toward the perforated mirror 45.

Figure 18:
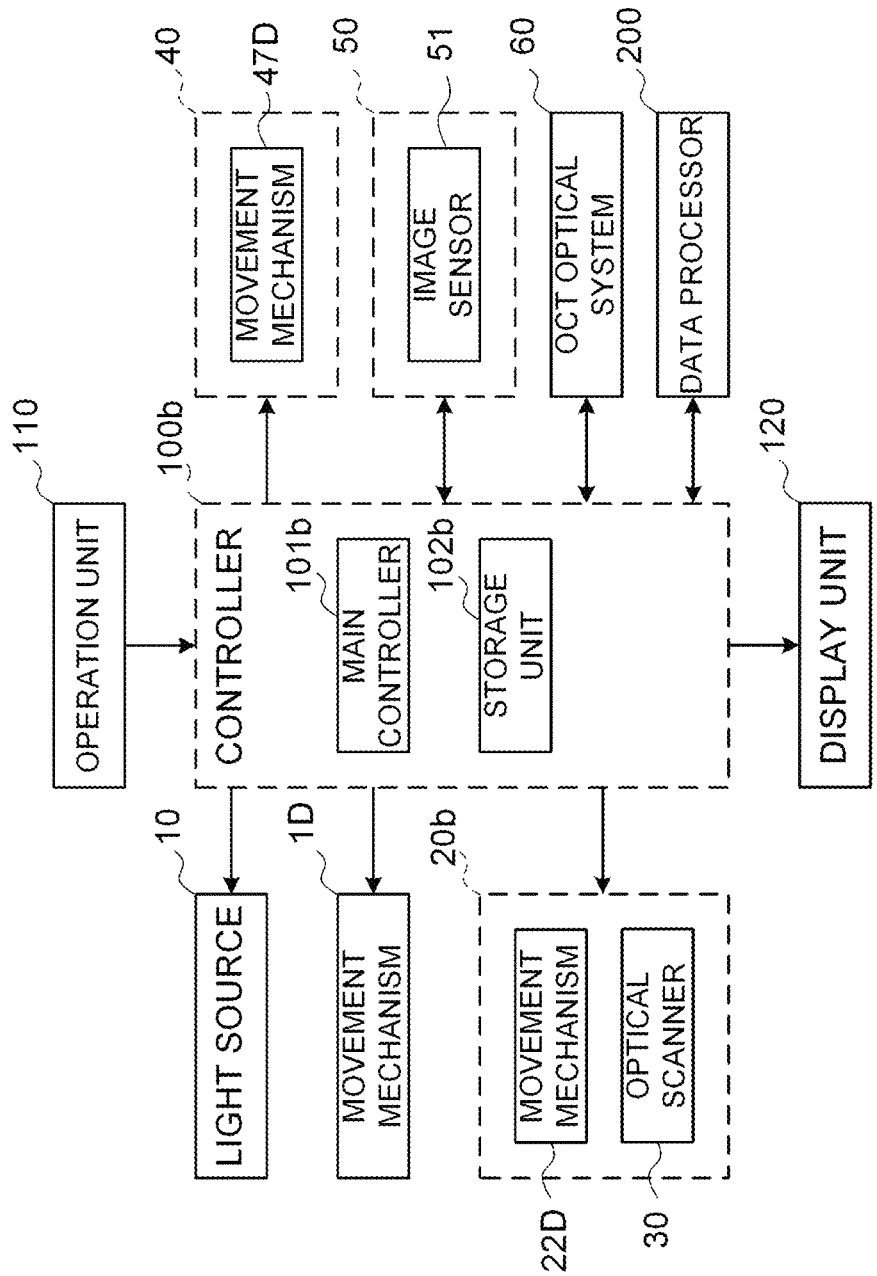
FIG. 18 is a diagram illustrating an example of a configuration of a control system of the ophthalmic apparatus according to the third embodiment.

FIG. 18 shows a block diagram of an example of the configuration of a control system of the ophthalmic apparatus 1b according to the third embodiment. In FIG. 18, parts similar to those in FIG. 11 are denoted by the same reference symbols, and description thereof is omitted as appropriate.

As shown in FIG. 18, the control system of the ophthalmic apparatus 1b is configured with a controller 100b as a center.

It should be noted at least a part of the configuration of the control system may be included in the ophthalmic apparatus 1b.

(Controller 100b)

The controller 100b controls each part of the ophthalmic apparatus 1b in the same way as the controller 100. The controller 100b includes a main controller 101b and a storage unit 102b. The main controller 101b includes a processor and executes the control processing of each part of the ophthalmic apparatus 1b by executing processing according to the program(s) stored in the storage unit 102b. (Main Controller 101b) The main controller 101b performs control for the light source 10, movement mechanism 1D, control for the illumination optical system 20b, control for the imaging optical system 40, control for the imaging device 50, control for the OCT optical system 60, and control for the data processor 200, in the same way as the main controller 101.

Examples of the control for the illumination optical system 20b include a control for the movement mechanism 22D, and a control for the optical scanner 30.

The movement mechanism 22D moves the slit 22 in the optical axis direction of the illumination optical system 20b. The main controller 101b can control the movement mechanism 22D in accordance with the state of the subject's eye E to arrange the slit 22 at the position corresponding to the state of the subject's eye E.

For example, the storage unit 102b stores second control information. In the second control information, the positions of the slit 22 on the optical axis of the illumination optical system 20b are associated with the dioptric powers in advance. The main controller 101b specifies the position of the slit 22 corresponding to the dioptric power by referring to the second control information, and controls the movement mechanism 22D so as to arrange the slit 22 at the specified position.

Examples of the control for the optical scanner 30 include a control of the scan range (scan start position and scan end position) and the scan speed.

The operation of the ophthalmic apparatus 1b according to the third embodiment is similar to the operation of the ophthalmic apparatus 1 according to the first embodiment. Thus, the detailed description of the operation will be omitted.

The movement mechanism 22D is an example of the "fourth movement mechanism" according to the embodiments.

As described above, according to the third embodiment, the same effects as in the first embodiment can be achieved by deflecting the illumination light using the optical scanner.

[Actions]

The ophthalmic apparatus, the method of controlling the ophthalmic apparatus, and a program according to the embodiments will be explained.

An ophthalmic apparatus (1, 1a, 1b) includes an illumination optical system (20, 20a, 20b), an imaging optical system (40, 40a), and a controller (100, main controller 101, 100b, main controller 101b). The illumination optical system is configured to generate illumination light using light from a light source (10), and to illuminate a changeable illumination region on a predetermined site (fundus Ef) of a subject's eye (E) with the illumination light having a light intensity corresponding to a size of the illumination region. The imaging optical system is configured to guide returning light of the illumination light from the subject's eye to a light receiving surface (SR) of an image sensor (51). The controller is configured to control the image sensor to set an opening range so as to overlap an illumination range (IP') of the returning light on the light receiving surface corresponding to the illumination region (IP) and to capture a light receiving result obtained by a light receiving element in the set opening range.

According to such an aspect, the illumination light is irradiated onto the illumination region in the predetermined site of the subject's eye, and the image sensor captures the light receiving result in the opening range set so as to overlap the illumination range of the returning light of the illumination light. Thereby, the predetermined site can be imaged at high speed with a simple configuration. In this case, the size of the illumination region is changeable, and the light intensity of the illumination light is changed in accordance with the changed size of the illumination region. This allows to change the light intensity of the returning light from the predetermined site in accordance with the size of the illumination region. As a result, the SNR of the light receiving result of the returning light can be improved in accordance with the size of the illumination region, and the image quality of the image formed based on the light receiving result of the returning light can be enhanced.

In some embodiments, the illumination optical system is configured to generate the illumination light so that the light intensity increases when the size of the illumination region is switched to a smaller size and that the light intensity decreases when the size of the illumination area is switched to a larger size.

According to such an aspect, the light intensity of the illumination light can be changed to be higher when the size of the illumination region is reduced. Thereby, the light intensity of the returning light from the predetermined site becomes higher. This allows to improve the SNR of the light receiving result of the returning light and to enhance the image quality of the image formed based on the light receiving result of the returning light. As a result, the predetermined site can be observed in detail and the images necessary for highly accurate tracking can be acquired.

In some embodiments, the illumination optical system is configured to change the light intensity of the illumination light so that an irradiance on an anterior segment of the subject's eye remains constant.

According to such an aspect, the SNR of the light receiving result of the returning light can be improved while limiting the light intensity of the illumination light incident on the subject's eye.

In some embodiments, the controller is configured to control the light source to change the light intensity.

According to such an aspect, the SNR of the light receiving result of the returning light can be improved and the image quality of the image formed based on the light receiving result of the returning light can be enhanced, with a simple control.

In some embodiments, the illumination optical system includes a neutral density filter (11) whose amount of light reduction is variable, the neutral density filter being placed in an optical path of the light from the light source, and the light intensity is changed by changing the amount of light reduction.

According to such an aspect, the SNR of the light receiving result of the returning light can be improved and the image quality of the image formed based on the light receiving result of the returning light can be enhanced, with a simple configuration.

In some embodiments, the controller is configured to control the illumination optical system so as to illuminate an illumination region with the illumination light, the illumination region corresponding to a designated imaging mode among two or more imaging modes (tracking mode, fundus imaging mode) that differ in the size of the illumination region at the predetermined site.

According to such an aspect, by designating the imaging mode, the illumination region with the size corresponding to the designated imaging mode can be illuminated with the illumination light having the light intensity corresponding to the size. This allows to improve the SNR of the light receiving result of the returning light in accordance with the imaging mode.

In some embodiments, the ophthalmic apparatus further includes an image forming unit (data processor 200) configured to form an image of the predetermined site based on a light receiving result obtained by the image sensor, and a first movement mechanism (movement mechanism 1D) configured to relatively move the subject's eye and the imaging optical system. In a first imaging mode (tracking mode), the controller is configured to control the image forming unit to form a first image based on a light receiving result obtained by illuminating a first illumination region corresponding to the first imaging mode with the illumination light, and to perform tracking control that moves the illumination optical system and the imaging optical system so as to follow the subject's eye by controlling the first movement mechanism. Further, in a second imaging mode (fundus imaging mode), the controller is configured to control the image forming unit to form a second image based on a light receiving result obtained by illuminating a second illumination region wider than the first illumination region with the illumination light, the second illumination region corresponding to the second imaging mode.

According to such an aspect, an ophthalmic apparatus capable of performing tracking control with high accuracy and of acquiring the wide-angle image with high quality, with a simple configuration can be provided.

In some embodiments, the controller is configured to capture the light receiving result using a rolling shutter method.

According to such an aspect, using the rolling shutter method, the SNR of the light receiving result of the returning light can be improved and the image quality of the image formed based on the light receiving result of the returning light can be enhanced, with a simple configuration.

In some embodiments, the ophthalmic apparatus further includes a perforated mirror (45) arranged at a position substantially conjugate optically to an iris of the subject's eye and having a hole that an optical axis of one of the illumination optical system and the imaging optical system passes through. The other of the illumination optical system and the imaging optical system is placed in a reflection direction of the perforated mirror. The illumination optical system includes: a light modulator (DMD 24) capable of being placed at a position substantially conjugate optically to the predetermined site, and configured to modulate the illumination light and to guide the modulated illumination light to the subject's eye; and an iris aperture (21) placed between the light source and the light modulator, and capable of being placed at a position substantially conjugate optically to the iris.

According to such an aspect, the illumination light for illuminating an arbitrary region on a predetermined site can be generated using the light modulator, and the generated illumination light can be efficiently entered into subject's eye with pupil division. Therefore, even when an inexpensive light source with a wide spread angle is used, the illumination intensity required for imaging the fundus can be secured with a simple configuration.

In some embodiments, the illumination optical system includes a first lens (relay lens 25) capable of being moved along an optical path of the illumination light modulated by the light modulator, and a second movement mechanism (movement mechanism 25D) configured to move the first lens along the optical path. The controller is configured to control the second movement mechanism in accordance with a dioptric power of the subject's eye.

According to such an aspect, the first lens is moved in accordance with the dioptric power of the subject's eye. This allows to arrange the light modulator at a position substantially conjugate optically to the iris of the subject's eye, regardless of the dioptric power of the subject's eye. Therefore, the light from the light source can be efficiently guided into the eye. As a result, even when an inexpensive light source with a wide spread angle is used, the illumination intensity required for imaging the fundus can be secured and high quality images of the subject's eye can be acquired without being affected by the condition of the subject's eye, with a simple configuration.

In some embodiments, the illumination optical system includes a second lens (relay lens 23) placed between the light modulator and the iris aperture, and capable of being moved along an optical path of the illumination light, and a third movement mechanism (movement mechanism 23D or movement mechanism 21D) configured to move the second lens or the iris aperture along the optical path of the illumination light. The controller is configured to control the third movement mechanism.

According to such an aspect, even when the position of the iris aperture is shifted from the position substantially conjugate optically to the iris of the subject's eye caused by the movement of the first lens, the shill caused by the movement of the second lens can be canceled. Therefore, the light from the light source can be efficiently guided into the eye.

In some embodiments, the ophthalmic apparatus further includes an optical path coupling member (beam splitter BS) configured to couple an optical path of the illumination optical system with an optical path of the imaging optical systems. The illumination optical system includes a light modulator (DMD 24) capable of being placed at a position substantially conjugate optically to the predetermined site, and configured to modulate the illumination light and to guide the modulated illumination light to the subject's eye.

According to such an aspect, the light from the light source can be entered into the subject's eye with a simple configuration, compared to the case where the perforated mirror and the iris aperture are provided.

In some embodiments, the illumination optical system includes a first lens (relay lens 25) capable of being moved along an optical path of the illumination light modulated by the light modulator, and a second movement mechanism (movement mechanism 25D) configured to move the first lens along the optical path. The controller is configured to control the second movement mechanism in accordance with a dioptric power of the subject's eye.

According to such an aspect, the first lens is moved in accordance with the dioptric power of the subject's eye. This allows to arrange the light modulator at a position substantially conjugate optically to the iris of the subject's eye, regardless of the dioptric power of the subject's eye. Therefore, the light from the light source can be efficiently guided into the eye. As a result, even when an inexpensive light source with a wide spread angle is used, the illumination intensity required for imaging the fundus can be secured and high quality images of the subject's eye can be acquired without being affected by the condition of the subject's eye, with a simple configuration.

In some embodiments, the ophthalmic apparatus further includes a perforated mirror (45) arranged at a position substantially conjugate optically to an iris of the subject's eye and having a hole that an optical axis of one of the illumination optical system and the imaging optical system passes through. The other of the illumination optical system and the imaging optical system is placed in a reflection direction of the perforated mirror. The illumination optical system includes an optical scanner (30), an iris aperture (21), and a slit (22). The optical scanner is capable of being placed at a position substantially conjugate optically to the iris, and is configured to deflect the illumination light and to guide the deflected illumination light to the subject's eye. The iris aperture is placed between the light source and the optical scanner and is capable of being placed at a position substantially conjugate optically to the iris. The slit is placed between the optical scanner and the iris aperture, having an aperture, and is capable of being placed at a position substantially conjugate optically to the predetermined site.

According to such an aspect, the illumination light for illuminating an arbitrary region on a predetermined site can be generated using the optical scanner, and the generated illumination light can be efficiently entered into subject's eye with pupil division. Therefore, even when an inexpensive light source with a wide spread angle is used, the illumination intensity required for imaging the fundus can be secured with a simple configuration.

In some embodiments, the ophthalmic apparatus further includes a fourth movement mechanism (movement mechanism 22D) configured to move the slit along an optical path of the illumination light, wherein the controller is configured to control the fourth movement mechanism in accordance with a dioptric power of the subject's eye.

According to such an aspect, the slit is moved in accordance with the dioptric power of the subject's eye. This allows to arrange the slit a position substantially conjugate optically to the predetermined site of the subject's eye, regardless of the dioptric power of the subject's eye. Therefore, the light from the light source can be efficiently guided into the eye. As a result, even when an inexpensive light source with a wide spread angle is used, the illumination intensity required for imaging the fundus can be secured and high quality images of the subject's eye can be acquired without being affected by the condition of the subject's eye, with a simple configuration.

In some embodiments, a method of controlling an ophthalmic apparatus 1s a method of controlling the ophthalmic apparatus including an illumination optical system (20, 20a, 20b), an imaging optical system (40, 40a). The illumination optical system is configured to generate illumination light using light from a light source (10), and to illuminate a subject's eye (E) with the illumination light. The imaging optical system is configured to guide returning light of the illumination light from the subject's eye to a light receiving surface (SR) of an image sensor (51). The method of controlling the ophthalmic apparatus includes an illumination region control step, a light intensity control step, and an image sensor control step. The illumination region control step is performed to change an illumination region of the illumination light on a predetermined site of the subject's eye. The light intensity control step is performed to change light intensity of the illumination light so as to have a light intensity corresponding to a size of the illumination region changed in the illumination region control step. The image sensor control step is performed to control the image sensor to set an opening range so as to overlap an illumination range of the returning light on the light receiving surface corresponding to the illumination region changed in the illumination region control step and to capture a light receiving result obtained by a light receiving element in the set opening range.

According to such an aspect, the illumination light is irradiated onto the illumination region in the predetermined site of the subject's eye, and the image sensor captures the light receiving result in the opening range set so as to overlap the illumination range of the returning light of the illumination light. Thereby, the predetermined site can be imaged at high speed with a simple configuration. In this case, the size of the illumination region is changeable, and the light intensity of the illumination light is changed in accordance with the changed size of the illumination region. This allows to change the light intensity of the returning light from the predetermined site in accordance with the size of the illumination region. As a result, the SNR of the light receiving result of the returning light can be improved in accordance with the size of the illumination region, and the image quality of the image formed based on the light receiving result of the returning light can be enhanced.

In some embodiments, the light intensity control step is performed to generate the illumination light so that the light intensity increases when the size of the illumination area is switched to a smaller size and that the light intensity decreases when the size of the illumination area is switched to a larger size.

According to such an aspect, the light intensity of the illumination light can be changed to be higher when the size of the illumination region is reduced. Thereby, the light intensity of the returning light from the predetermined site becomes higher. This allows to improve the SNR of the light receiving result of the returning light and to enhance the image quality of the image formed based on the light receiving result of the returning light. As a result, the predetermined site can be observed in detail and the images necessary for highly accurate tracking can be acquired.

In some embodiments, the light intensity control step is performed to change the light intensity of the illumination light so that an irradiance on an anterior segment of the subject's eye remains constant.

According to such an aspect, the SNR of the light receiving result of the returning light can be improved while limiting the light intensity of the illumination light incident on the subject's eye.

In some embodiments, the light intensity control step is performed to control the light source to change the light intensity.

According to such an aspect, the SNR of the light receiving result of the returning light can be improved and the image quality of the image formed based on the light receiving result of the returning light can be enhanced, with a simple control.

In some embodiments, the illumination optical system includes a neutral density filter (11) whose amount of light reduction is variable, the neutral density filter being placed in an optical path of the light from the light source. The light intensity control step is performed to change the light intensity by changing the amount of light reduction.

According to such an aspect, the SNR of the light receiving result of the returning light can be improved and the image quality of the image formed based on the light receiving result of the returning light can be enhanced, with a simple configuration.

In some embodiments, the illumination region control step is performed to control the illumination optical system so as to illuminate an illumination region with the illumination light, the illumination region corresponding to a designated imaging mode among two or more imaging modes (tracking mode, fundus imaging mode) that differ in the illumination region at the predetermined site.

According to such an aspect, by designating the imaging mode, the illumination region with the size corresponding to the designated imaging mode can be illuminated with the illumination light having the light intensity corresponding to the size. This allows to improve the SNR of the light receiving result of the returning light in accordance with the imaging mode.

In some embodiments, the ophthalmic apparatus includes a first movement mechanism (movement mechanism 1D) configured to relatively move the subject's eye and the imaging optical system. The method of controlling the ophthalmic apparatus includes a first illumination region control step, a first light intensity control step, a first image forming step, a tracking control step, a second illumination region control step, a second light intensity control step, and a second image forming step. The first illumination region control step is performed to illuminate a first illumination region corresponding to a first imaging mode with the illumination light, in the first imaging mode (tracking mode). The first light intensity control step is performed to change a light intensity of the illumination light into a light intensity corresponding to a size of the illumination region changed in the first illumination region control step. The first image forming step is performed to form a first image of the predetermined site using a light receiving result of returning light from the illumination region illuminated with the illumination light having the light intensity changed in the first light intensity control step. The tracking control step is performed to perform tracking control that moves the illumination optical system and the imaging optical system so as to follow the subject's eye by controlling the first movement mechanism based on the first image formed in the first image forming step. The second illumination region control step is performed to illuminate a second illumination region wider than the first illumination region with the illumination light, the second illumination region corresponding to a second imaging mode, in the second imaging mode (fundus imaging mode). The second light intensity control step is performed to change light intensity of the illumination light into the light intensity corresponding to a size of the illumination region changed in the second illumination region control step. The second image forming step is performed to form a second image of the predetermined site using a light receiving result of returning light from the illumination region illuminated with the illumination light having the light intensity changed in the second light intensity control step.

According to such an aspect, the tracking control with high accuracy can be performed and the wide-angle image with high quality can be acquired, with a simple configuration.

In some embodiments, the image sensor control step is performed to capture the light receiving result using a rolling shutter method.

According to such an aspect, using the rolling shutter method, the SNR of the light receiving result of the returning light can be improved and the image quality of the image formed based on the light receiving result of the returning light can be enhanced, with a simple configuration.

In some embodiments, a program is a program of causing a computer to execute each step of the method of the ophthalmic apparatus of any one of the above.

According to such a program, the illumination light is irradiated onto the illumination region in the predetermined site of the subject's eye, and the image sensor captures the light receiving result in the opening range set so as to overlap the illumination range of the returning light of the illumination light. Thereby, the predetermined site can be imaged at high speed with a simple configuration. In this case, the size of the illumination region is changeable, and the light intensity of the illumination light is changed in accordance with the changed size of the illumination region. This allows to change the light intensity of the returning light from the predetermined site in accordance with the size of the illumination region. As a result, the SNR of the light receiving result of the returning light can be improved in accordance with the size of the illumination region, and the image quality of the image formed based on the light receiving result of the returning light can be enhanced.

The above-described some embodiments or the modification examples thereof are merely examples for carrying out the present invention. Those who intend to implement the present invention can apply any modification, omission, addition, or the like within the scope of the gist of the present invention.

In some embodiments, a program for causing a computer to execute the method of controlling the ophthalmic apparatus described above is provided. Such a program can be stored in any non-transitory computer-readable recording medium. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The configurations described in the first to the third embodiments can be combined as desired.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ophthalmic apparatus, comprising:
   an illumination optical system configured to generate illumination light using light from a light source, and to illuminate a changeable illumination region on a predetermined site of a subject's eye with the illumination light having a light intensity corresponding to a size of the illumination region;
   an imaging optical system configured to guide returning light of the illumination light from the subject's eye to a light receiving surface of an image sensor;
   a controller configured to control the image sensor to set a readout range that is a range of light receiving elements to be read out so as to overlap an illumination range of the returning light on the light receiving surface corresponding to the illumination region and to capture a light receiving result obtained by a light receiving element in the set readout range; and
   a perforated mirror arranged at a position substantially conjugate optically to an iris of the subject's eye and having a hole that an optical axis of one of the illumination optical system and the imaging optical system passes through, wherein
   the other of the illumination optical system and the imaging optical system is placed in a reflection direction of the perforated mirror, and
   the illumination optical system includes:
      a light modulator capable of being placed at a position substantially conjugate optically to the predetermined site, and configured to modulate the illumination light and to guide the modulated illumination light to the subject's eye; and
      an iris aperture placed between the light source and the light modulator, and capable of being placed at a position substantially conjugate optically to the iris of the subject's eye, wherein
   the illumination optical system includes a first lens capable of being moved along an optical path of the illumination light modulated by the light modulator,
   the controller is configured to control a movement of the first lens along the optical path in accordance with a dioptric power of the subject's eye,
   the illumination optical system includes a second lens placed between the light modulator and the iris aperture, and capable of being moved along an optical path of the illumination light, and
   the controller is configured to control a movement of the iris aperture along the optical path of the illumination light.

2. The ophthalmic apparatus of claim 1, wherein
the illumination optical system is configured to generate the illumination light so that the light intensity increases when the size of the illumination region is switched to a smaller size and that the light intensity decreases when the size of the illumination area is switched to a larger size.

3. The ophthalmic apparatus of claim 1, wherein
the illumination optical system is configured to change the light intensity of the illumination light so that an irradiance on an anterior segment of the subject's eye remains constant.

4. The ophthalmic apparatus of claim 1, wherein
the controller is configured to control the light source to change the light intensity.

5. The ophthalmic apparatus of claim 1, wherein
the illumination optical system includes a neutral density filter whose amount of light reduction is variable, the neutral density filter being placed in an optical path of the light from the light source, and the light intensity is changed by changing the amount of light reduction.

6. The ophthalmic apparatus of claim 1, wherein
the controller is configured to control the illumination optical system so as to illuminate an illumination region with the illumination light, the illumination region corresponding to a designated imaging mode among two or more imaging modes that differ in the size of the illumination region at the predetermined site.

7. The ophthalmic apparatus of claim 6, further comprising
an image forming unit configured to form an image of the predetermined site based on a light receiving result obtained by the image sensor, wherein
in a first imaging mode, the controller is configured to control the image forming unit to form a first image based on a light receiving result obtained by illuminating a first illumination region corresponding to the first imaging mode with the illumination light, and to perform tracking control that moves the illumination optical system and the imaging optical system so as to follow the subject's eye by controlling a relative distance between the subject's eye and the imaging optical system, and
in a second imaging mode, the controller is configured to control the image forming unit to form a second image based on a light receiving result obtained by illuminating a second illumination region wider than the first illumination region with the illumination light, the second illumination region corresponding to the second imaging mode.

8. The ophthalmic apparatus of claim 1, wherein
the controller is configured to capture the light receiving result using a rolling shutter method.

9. The ophthalmic apparatus of claim 1, further comprising
an optical path coupling member configured to couple an optical path of the illumination optical system with an optical path of the imaging optical systems, wherein
the illumination optical system includes a light modulator capable of being placed at a position substantially conjugate optically to the predetermined site, and configured to modulate the illumination light and to guide the modulated illumination light to the subject's eye.

10. The ophthalmic apparatus of claim 9, wherein
the illumination optical system includes a first lens capable of being moved along an optical path of the illumination light modulated by the light modulator, and
the controller is configured to control a movement of the first lens along the optical path in accordance with a dioptric power of the subject's eye.

11. The ophthalmic apparatus of claim 1, further comprising
a perforated mirror arranged at a position substantially conjugate optically to an iris of the subject's eye and having a hole that an optical axis of one of the illumination optical system and the imaging optical system passes through, wherein
the other of the illumination optical system and the imaging optical system is placed in a reflection direction of the perforated mirror, and
the illumination optical system includes:
an optical scanner capable of being placed at a position substantially conjugate optically to the iris of the subject's eye, and configured to deflect the illumination light and to guide the deflected illumination light to the subject's eye;
an iris aperture placed between the light source and the optical scanner and capable of being placed at a position substantially conjugate optically to the iris of the subject's eye; and
a slit placed between the optical scanner and the iris aperture, having an aperture, and capable of being placed at a position substantially conjugate optically to the predetermined site.

12. The ophthalmic apparatus of claim 11, further comprising
the controller is configured to control a movement of the slit along an optical path of the illumination light in accordance with a dioptric power of the subject's eye.

13. A method of controlling an ophthalmic apparatus comprising:
an illumination optical system configured to generate illumination light using light from a light source, and to illuminate a subject's eye with the illumination light; and
an imaging optical system configured to guide returning light of the illumination light from the subject's eye to a light receiving surface of an image sensor,
the method comprising:
an illumination region control step of changing an illumination region of the illumination light on a predetermined site of the subject's eye;
a light intensity control step of changing light intensity of the illumination light so as to have a light intensity corresponding to a size of the illumination region changed in the illumination region control step;
an image sensor control step of controlling the image sensor to set a readout range that is a range of light receiving elements to be read out so as to overlap an illumination range of the returning light on the light receiving surface corresponding to the illumination region changed in the illumination region control step and to capture a light receiving result obtained by a light receiving element in the set readout range;
arranging a perforated mirror at a position substantially conjugate optically to an iris of the subject's eye, the perforated mirror having a hole that an optical axis of one of the illumination optical system and the imaging optical system passes through;
placing the other of the illumination optical system and the imaging optical system in a reflection direction of the perforated mirror, wherein
the illumination optical system includes:
a light modulator capable of being placed at a position substantially conjugate optically to the predetermined site, and configured to modulate the illumination light and to guide the modulated illumination light to the subject's eye; and
an iris aperture placed between the light source and the light modulator, and capable of being placed at a position substantially conjugate optically to the iris of the subject's eye, the method further comprising:
controlling a movement of the first lens along the optical path of the illumination light modulated by the light modulator in accordance with a dioptric power of the subject's eye, wherein the illumination optical system includes a second lens placed between the light modulator and the iris aperture, the second lens being capable of being moved along an optical path of the illumination light, and the method further comprising:
controlling a movement of the iris aperture along the optical path of the illumination light.

14. The method of controlling the ophthalmic apparatus of claim 13, wherein
the light intensity control step is performed to generate the illumination light so that the light intensity increases when the size of the illumination area is switched to a smaller size and that the light intensity decreases when the size of the illumination area is switched to a larger size.

15. The method of controlling the ophthalmic apparatus of claim 13, wherein
the light intensity control step is performed to change the light intensity of the illumination light so that an irradiance on an anterior segment of the subject's eye remains constant.

16. The method of controlling the ophthalmic apparatus of claim 13, wherein
the light intensity control step is performed to control the light source to change the light intensity.

17. The method of controlling the ophthalmic apparatus of claim 13, wherein
the illumination optical system includes a neutral density filter whose amount of light reduction is variable, the neutral density filter being placed in an optical path of the light from the light source, and
the light intensity control step is performed to change the light intensity by changing the amount of light reduction.

18. The method of controlling the ophthalmic apparatus of claim 13, wherein
the illumination region control step is performed to control the illumination optical system so as to illuminate an illumination region with the illumination light, the illumination region corresponding to a designated imaging mode among two or more imaging modes that differ in the illumination region at the predetermined site.

19. The method of controlling the ophthalmic apparatus of claim 18, further comprising:
a first illumination region control step of illuminating a first illumination region corresponding to a first imaging mode with the illumination light, in the first imaging mode;
a first light intensity control step of changing a light intensity of the illumination light into a light intensity corresponding to a size of the illumination region changed in the first illumination region control step;
a first image forming step of forming a first image of the predetermined site using a light receiving result of returning light from the illumination region illuminated with the illumination light having the light intensity changed in the first light intensity control step;
a tracking control step of performing tracking control that moves the illumination optical system and the imaging optical system so as to follow the subject's eye by controlling a relative distance between the subject's eye and the imaging optical system based on the first image formed in the first image forming step;
a second illumination region control step of illuminating a second illumination region wider than the first illumination region with the illumination light, the second illumination region corresponding to a second imaging mode, in the second imaging mode;
a second light intensity control step of changing light intensity of the illumination light into the light intensity corresponding to a size of the illumination region changed in the second illumination region control step; and
a second image forming step of forming a second image of the predetermined site using a light receiving result of returning light from the illumination region illuminated with the illumination light having the light intensity changed in the second light intensity control step.

20. The method of controlling the ophthalmic apparatus of claim 13, wherein
the image sensor control step is performed to capture the light receiving result using a rolling shutter method.

21. A computer readable non-transitory recording medium in which a program for causing a computer to execute each step of the method of controlling the ophthalmic apparatus of claim 13 is recorded.

* * * * *